(12) United States Patent
Hinuma et al.

(10) Patent No.: US 7,138,249 B2
(45) Date of Patent: Nov. 21, 2006

(54) SCREENING METHOD

(75) Inventors: Shuji Hinuma, Tsukuba (JP); Yasushi Shintani, Toyonaka (JP); Masaki Hosoya, Tsuchiura (JP); Ryo Fujii, Tsukuba (JP); Takeo Moriya, Minou (JP); Hideki Matsui, Tsukuba (JP); Shoichi Okubo, Ushiku (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 397 days.

(21) Appl. No.: 10/203,015

(22) PCT Filed: Feb. 2, 2001

(86) PCT No.: PCT/JP01/00746

§ 371 (c)(1),
(2), (4) Date: Sep. 23, 2002

(87) PCT Pub. No.: WO01/57524

PCT Pub. Date: Aug. 9, 2001

(65) Prior Publication Data

US 2004/0152136 A1    Aug. 5, 2004

(30) Foreign Application Priority Data

| Feb. 4, 2000 | (JP) | ............................. 2000-032773 |
| Feb. 24, 2000 | (JP) | ............................. 2000-052252 |
| Mar. 30, 2000 | (JP) | ............................. 2000-097896 |
| Jun. 19, 2000 | (JP) | ............................. 2000-187536 |

(51) Int. Cl.
*G01N 33/566* (2006.01)

(52) U.S. Cl. ........................... 435/7.21; 436/501

(58) Field of Classification Search .............. 435/7.2, 435/69.1, 252.3, 320.1; 530/350; 536/23.5; 436/501
See application file for complete search history.

(56) References Cited

U.S. PATENT DOCUMENTS

2003/0148450 A1 * 8/2003 Chen et al. ............... 435/69.1

FOREIGN PATENT DOCUMENTS

| WO | WO 99/55732 | 11/1999 |
| WO | WO 00/02919 | 1/2000 |
| WO | WO 00/22131 | 4/2000 |
| WO | WO 00/31258 | 6/2000 |
| WO | WO 01/40797 | 6/2001 |
| WO | WO 01/44297 | 6/2001 |
| WO | WO 01/81418 | 11/2001 |

OTHER PUBLICATIONS

M. Hosoya, et al. "Identification and Functional Characterization of a Novel Subtype of Neuromedin U Receptor" The Journal of Biological Chemistry 275(38): 29528-32 (Sep. 22, 2000).
N. Minamino, et al. "Neuromedin U-8 and U-25: Novel Uterus Stimulating and Hypertensive Peptides Identified in Porcine Spinal Cord" Biochemical and Biophysical Research Communications 130(3): 1078-85 (Aug. 15, 1985).
L. Malendowicz, et al. "Effects of Neuromedin U-8 on the Rat Pituitary-Adrenocortical Axis" In Vivo 7:419-22(1993).
D. Brown, et al. "Neuromedin U Octapeptide Alters Ion Transport in Porcine Jejunum" European Journal of Pharmacology 155:159-62 (1988).
S. Sumi, et al. "Effect of Syntheic Neuromedin U-8 and U-25, Novel Peptides Identified in Porcine Spinal Cord, on Splanchnic Circulation in Dogs" Life Sciences 41:1585-90(1987).
C. Tan, et al. "Cloning and Characterization of a Human and Murine T-Cell Orphan G-Protein-Coupled Receptor Similar to the Growth Hormone Secretagogue and Neurotensin Receptors" GENOMICS 52:223-29(1998).
K. Kulju, et al. "Cloning and Characterization of Two Human G Protein-Coupled Receptor Genes (GPR38 and GPR39) Related to the Growth Hormone Secretagogue and Neurotensin Receptors" GENOMICS 46:426-34(1997).
A. Howard, et al. "Identification of Receptors for Neuromedin U and Its Role in Feeding" NATURE 406:70-74(Jul. 6, 2000).
Kirian A. Nandha, et al., "Neuromedin U—An Overview", Biomedical Research, (1993), pp. 71-76, vol. 14, Supplement 3; XP-001052975.
Rita Raddatz, et al., "Identification and Characterizaiton of two Neuromedin U Receptors Differentially Expressed in Peripheral Tissues and the Central Nervous System", The Journal of Biological Chemistry (2000), pp. 32452-32459, vol. 275, No. 42, XP002163227.
Ryo Fujii, et al., "Identification of Neuromedin U as the Cognate Ligand of the Orphan G Protein-coupled Receptor FM-3", The Journal of Biological Chemistry, (2000), pp. 21068-21074, vol. 275, No. 28, XP-002163226.
Funes, S. et al., Cloning and characterization of murine neuromedin U receptors, PEPTIDES 23 (2002) 1607-1615.

* cited by examiner

*Primary Examiner*—John Ulm
(74) *Attorney, Agent, or Firm*—Elaine M. Ramesh; Mark Chao

(57) ABSTRACT

The screening method for a compound or a salt thereof that alters the binding property between Neuromedin U or a salt thereof and TGR-1 or a salt thereof, characterized by using Neuromedin U, a derivative thereof or a salt thereof and TGR-1 or a salt thereof, can be useful for screening a therapeutic and/or prophylactic agent for hypertension and stress-related diseases, etc. A TGR-1 antagonist can be useful as a therapeutic and/or prophylactic agent for hypertension and stress-related diseases, etc.

10 Claims, 2 Drawing Sheets

Fig.2

SEQUENCE LISTING

```
<160> NUMBER OF SEQ ID NOS: 22

<210> SEQ ID NO 1
<211> LENGTH: 415
<212> TYPE: PRT
<213> ORGANISM: Human

<400> SEQUENCE: 1

Met Ser Gly Met Glu Lys Leu Gln Asn Ala Ser Trp Ile Tyr Gln Gln
1               5                   10                  15

Lys Leu Glu Asp Pro Phe Gln Lys His Leu Asn Ser Thr Glu Glu Tyr
            20                  25                  30

Leu Ala Phe Leu Cys Gly Pro Arg Arg Ser His Phe Phe Leu Pro Val
        35                  40                  45

Ser Val Val Tyr Val Pro Ile Phe Val Val Gly Val Ile Gly Asn Val
    50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Leu Val Leu Leu
                85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
```

```
              180             185             190
Pro Asn Gly Ser Leu Val Pro Gly Ser Ala Thr Cys Thr Val Ile Lys
        195                 200                 205

Pro Met Trp Ile Tyr Asn Phe Ile Ile Gln Val Thr Ser Phe Leu Phe
    210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Phe Val
            260                 265                 270

Leu Val Leu Val Phe Ala Ile Cys Trp Ala Pro Phe His Ile Asp Arg
    275                 280                 285

Leu Phe Phe Ser Phe Val Glu Glu Trp Ser Glu Ser Leu Ala Ala Val
    290                 295                 300

Phe Asn Leu Val His Val Ser Gly Val Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
            340                 345                 350

His Asp Pro Gln Leu Pro Pro Ala Gln Arg Asn Ile Phe Leu Thr Glu
        355                 360                 365

Cys His Phe Val Glu Leu Thr Glu Asp Ile Gly Pro Gln Phe Pro Cys
    370                 375                 380

Gln Ser Ser Met His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 2
<211> LENGTH: 1245
<212> TYPE: DNA
<213> ORGANISM: Human

<400> SEQUENCE: 2
atgtcaggga tggaaaaact tcagaatgct tcctggatct accagcagaa actagaagat    60
ccattccaga aacacctgaa cagcaccgag gagtatctgg ccttcctctg cggacctcgg   120
cgcagccact tcttcctccc cgtgtctgtg gtgtatgtgc caattttttgt ggtgggggtc   180 attggcaatg tcctggtgtg cctggtgatt ctgcagcacc aggctatgaa gacgcccacc   240
aactactacc tcttcagcct ggcggtctct gacctcctgg tcctgctcct ggaatgccc    300 ctggaggtct atgagatgtg cgcaactac ccttttcttgt cgggcccgt gggctgctac   360 ttcaagacgg ccctctttga gaccgtgtgc ttcgcctcca tcctcagcat caccaccgtc   420
agcgtggagc gctacgtggc catcctacac ccgttccgcg ccaaactgca gagcacccgg   480
cgccgggccc tcaggatcct cggcatcgtc tggggcttct ccgtgctctt ctccctgccc   540
aacaccagca tccatggcat caagttccac tacttcccca tgggtccct ggtcccaggt    600 tcggccacct gtacggtcat caagcccatg tggatctaca atttcatcat ccaggtcacc   660
tccttcctat tctacctcct ccccatgact gtcatcagtg tcctctacta cctcatggca   720
ctcagactaa agaaagacaa atctcttgag gcagatgaag ggaatgcaaa tattcaaaga   780
ccctgcagaa aatcagtcaa caagatgctg tttgtcttgg tcttagtgtt tgctatctgt   840
```

```
tgggccccgt tccacattga ccgactcttc ttcagctttg tggaggagtg gagtgaatcc      900
ctggctgctg tgttcaacct cgtccatgtg gtgtcaggtg tcttcttcta cctgagctca      960
gctgtcaacc ccattatcta taacctactg tctcgccgct tccaggcagc attccagaat     1020
gtgatctctt ctttccacaa acagtggcac tcccagcatg acccacagtt gccacctgcc     1080
cagcggaaca tcttcctgac agaatgccac tttgtggagc tgaccgaaga tataggtccc     1140
caattcccat gtcagtcatc catgcacaac tctcacctcc aacagccct ctctagtgaa      1200 cagatgtcaa gaacaaacta tcaaagcttc cactttaaca aaacc                     1245
```

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
gtcgacttaa tgtcagggat ggaaaaactt      30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
actagttcag gttttgttaa agtggaagct      30

<210> SEQ ID NO 5
<211> LENGTH: 8
<212> TYPE: PRT
<213> ORGANISM: Pig

<400> SEQUENCE: 5

Tyr Phe Leu Phe Arg Pro Arg Asn
1               5               8

<210> SEQ ID NO 6
<211> LENGTH: 8
<212> TYPE: PRT
<213> ORGANISM: Dog

<400> SEQUENCE: 6

Glu Phe Leu Phe Arg Pro Arg Asn
1               5               8

<210> SEQ ID NO 7
<211> LENGTH: 9
<212> TYPE: PRT
<213> ORGANISM: Chicken

<400> SEQUENCE: 7

Gly Tyr Phe Phe Phe Arg Pro Arg Asn
1               5               9

<210> SEQ ID NO 8
<211> LENGTH: 9
<212> TYPE: PRT
<213> ORGANISM: Guinea pig

<400> SEQUENCE: 8

```
Gly Tyr Phe Leu Phe Arg Pro Arg Asn
1               5                   9

<210> SEQ ID NO 9
<211> LENGTH: 23
<212> TYPE: PRT
<213> ORGANISM: Rat

<400> SEQUENCE: 9

Tyr Lys Val Asn Glu Tyr Gln Gly Pro Val Ala Pro Ser Gly Gly Phe
1               5                   10                  15

Phe Leu Phe Arg Pro Arg Asn
            20          23

<210> SEQ ID NO 10
<211> LENGTH: 23
<212> TYPE: PRT
<213> ORGANISM: Frog

<400> SEQUENCE: 10

Ser Asp Glu Glu Val Gln Val Pro Gly Gly Val Ile Ser Asn Gly Tyr
1               5                   10                  15

Phe Leu Phe Arg Pro Arg Asn
            20          23

<210> SEQ ID NO 11
<211> LENGTH: 25
<212> TYPE: PRT
<213> ORGANISM: Human

<400> SEQUENCE: 11

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 12
<211> LENGTH: 25
<212> TYPE: PRT
<213> ORGANISM: Pig

<400> SEQUENCE: 12

Phe Leu Val Asp Glu Glu Phe Gln Gly Pro Ile Val Ser Gln Asn Arg
1               5                   10                  15

Arg Tyr Phe Leu Phe Arg Pro Arg Asn
            20                  25

<210> SEQ ID NO 13
<211> LENGTH: 25
<212> TYPE: PRT
<213> ORGANISM: Dog

<400> SEQUENCE: 13

Phe Arg Leu Asp Glu Glu Phe Gln Gly Pro Ile Ala Ser Gln Val Arg
1               5                   10                  15

Arg Gln Phe Leu Phe Arg Pro Arg Asn
            20                  25

<210> SEQ ID NO 14
<211> LENGTH: 25
<212> TYPE: PRT
<213> ORGANISM: Chicken
```

```
<400> SEQUENCE: 14

Tyr Lys Val Asp Glu Asp Leu Gln Gly Ala Gly Gly Ile Gln Ser Arg
1               5                   10                  15

Gly Tyr Phe Phe Phe Arg Pro Arg Asn
            20                  25

<210> SEQ ID NO 15
<211> LENGTH: 25
<212> TYPE: PRT
<213> ORGANISM: Frog

<400> SEQUENCE: 15

Leu Lys Pro Asp Glu Glu Leu Gln Gly Pro Gly Gly Val Leu Ser Arg
1               5                   10                  15

Gly Tyr Phe Val Phe Arg Pro Arg Asn
            20                  25

<210> SEQ ID NO 16
<211> LENGTH: 5
<212> TYPE: PRT
<213> ORGANISM: Human

<400> SEQUENCE: 16

Phe Arg Pro Arg Asn
1               5

<210> SEQ ID NO 17
<211> LENGTH: 415
<212> TYPE: PRT
<213> ORGANISM: Human

<400> SEQUENCE: 17

Met Ser Gly Met Glu Lys Leu Gln Asn Ala Ser Trp Ile Tyr Gln Gln
1               5                   10                  15

Lys Leu Glu Asp Pro Phe Gln Lys His Leu Asn Ser Thr Glu Glu Tyr
            20                  25                  30

Leu Ala Phe Leu Cys Gly Pro Arg Arg Ser His Phe Phe Leu Pro Val
        35                  40                  45

Ser Val Val Tyr Val Pro Ile Phe Val Val Gly Val Ile Gly Asn Val
    50                  55                  60

Leu Val Cys Leu Val Ile Leu Gln His Gln Ala Met Lys Thr Pro Thr
65                  70                  75                  80

Asn Tyr Tyr Leu Phe Ser Leu Ala Val Ser Asp Leu Leu Val Leu Leu
                85                  90                  95

Leu Gly Met Pro Leu Glu Val Tyr Glu Met Trp Arg Asn Tyr Pro Phe
            100                 105                 110

Leu Phe Gly Pro Val Gly Cys Tyr Phe Lys Thr Ala Leu Phe Glu Thr
        115                 120                 125

Val Cys Phe Ala Ser Ile Leu Ser Ile Thr Thr Val Ser Val Glu Arg
    130                 135                 140

Tyr Val Ala Ile Leu His Pro Phe Arg Ala Lys Leu Gln Ser Thr Arg
145                 150                 155                 160

Arg Arg Ala Leu Arg Ile Leu Gly Ile Val Trp Gly Phe Ser Val Leu
                165                 170                 175

Phe Ser Leu Pro Asn Thr Ser Ile His Gly Ile Lys Phe His Tyr Phe
            180                 185                 190

Pro Asn Gly Ser Leu Val Pro Gly Ser Ala Thr Cys Thr Val Ile Lys
```

```
                195                 200                 205
Pro Met Trp Ile Tyr Asn Phe Ile Ile Gln Val Thr Ser Phe Leu Phe
        210                 215                 220

Tyr Leu Leu Pro Met Thr Val Ile Ser Val Leu Tyr Tyr Leu Met Ala
225                 230                 235                 240

Leu Arg Leu Lys Lys Asp Lys Ser Leu Glu Ala Asp Glu Gly Asn Ala
                245                 250                 255

Asn Ile Gln Arg Pro Cys Arg Lys Ser Val Asn Lys Met Leu Leu Val
                260                 265                 270

Leu Val Leu Val Phe Ala Ile Cys Trp Ala Pro Phe His Ile Asp Arg
            275                 280                 285

Leu Phe Phe Ser Phe Val Glu Glu Trp Thr Glu Ser Leu Ala Ala Val
        290                 295                 300

Phe Asn Leu Val His Val Val Ser Gly Val Leu Phe Tyr Leu Ser Ser
305                 310                 315                 320

Ala Val Asn Pro Ile Ile Tyr Asn Leu Leu Ser Arg Arg Phe Gln Ala
                325                 330                 335

Ala Phe Gln Asn Val Ile Ser Ser Phe His Lys Gln Trp His Ser Gln
            340                 345                 350

His Asp Pro Gln Leu Pro Pro Ala Gln Arg Asn Ile Phe Leu Thr Glu
        355                 360                 365

Cys His Phe Val Glu Leu Thr Glu Asp Ile Gly Pro Gln Phe Pro Cys
    370                 375                 380

Gln Ser Ser Val His Asn Ser His Leu Pro Thr Ala Leu Ser Ser Glu
385                 390                 395                 400

Gln Met Ser Arg Thr Asn Tyr Gln Ser Phe His Phe Asn Lys Thr
                405                 410                 415

<210> SEQ ID NO 18
<211> LENGTH: 1245
<212> TYPE: DNA
<213> ORGANISM: Human

<400> SEQUENCE: 18
atgtcaggga tggaaaaact tcagaatgct tcctggatct accagcagaa actagaagat      60
ccattccaga aacacctgaa cagcaccgag gagtatctgg ccttcctctg cggacctcgg     120
cgcagccact tcttcctccc cgtgtctgtg gtgtatgtgc aattttttgt ggtgggggtc     180
attggcaatg tcctggtgtg cctggtgatt ctgcagcacc aggctatgaa gacgcccacc     240
aactactacc tcttcagcct ggcggtctct gacctcctgg tcctgctcct tggaatgccc     300
ctggaggtct atgagatgtg cgcaactac cctttcttgt tcgggcccgt gggctgctac     360
ttcaagacgg ccctctttga ccgtgtgc ttcgcctcca tcctcagcat caccaccgtc     420
agcgtggagc gctacgtggc catcctacac ccgttccgcg ccaaactgca gagcacccgg     480
cgccgggccc tcaggatcct cggcatcgtc tggggcttct ccgtgctctt ctccctgccc     540
aacaccagca tccatggcat caagttccac tacttcccca tgggtccct ggtcccaggt     600 tcggccacct gtacggtcat caagcccatg tggatctaca atttcatcat ccaggtcacc     660
tccttcctat tctacctcct ccccatgact gtcatcagtg tcctctacta cctcatggca     720
ctcagactaa agaaagacaa atctcttgag gcagatgaag ggaatgcaaa tattcaaaga     780
ccctgcagaa aatcagtcaa caagatgctg cttgtcttgg tcttagtgtt tgctatctgt     840
tgggccccgt tccacattga ccgactcttc ttcagctttg tggaggagtg gactgaatcc     900
```

```
ctggctgctg tgttcaacct cgtccatgtg gtgtcaggtg tcttattcta cctgagctca       960
gctgtcaacc ccattatcta taacctactg tctcgccgct tccaggcagc attccagaat      1020
gtgatctctt ctttccacaa acagtggcac tcccagcatg acccacagtt gccacctgcc      1080
cagcggaaca tcttcctgac agaatgccac tttgtggagc tgaccgaaga tataggtccc      1140
caattcccat gtcagtcatc cgtgcacaac tctcacctcc caacagccct ctctagtgaa      1200
cagatgtcaa gaacaaacta tcaaagcttc cactttaaca aaacc                      1245
```

<210> SEQ ID NO 19
<211> LENGTH: 29
<212> TYPE: DNA
<213> ORGANISM: Artificial Sequence
<220> FEATURE:
<223> OTHER INFORMATION: primer

<400> SEQUENCE: 19

```
ctgatgctat cctttcactc tctcagacc                                          29
```

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20

```
tccttgcagt tttggcacat agatgga                                            27
```

<210> SEQ ID NO 21
<211> LENGTH: 395
<212> TYPE: PRT
<213> ORGANISM: Rat

<400> SEQUENCE: 21

```
Met Gly Lys Leu Glu Asn Ala Ser Trp Ile His Asp Pro Leu Met Lys
 1               5                  10                  15

Tyr Leu Asn Ser Thr Glu Glu Tyr Leu Ala His Leu Cys Gly Pro Lys
            20                  25                  30

Arg Ser Asp Leu Ser Leu Pro Val Ser Val Ala Tyr Ala Leu Ile Phe
        35                  40                  45

Leu Val Gly Val Met Gly Asn Leu Leu Val Cys Met Val Ile Val Arg
    50                  55                  60

His Gln Thr Leu Lys Thr Pro Thr Asn Tyr Tyr Leu Phe Ser Leu Ala
65                  70                  75                  80

Val Ser Asp Leu Leu Val Leu Leu Gly Met Pro Leu Glu Ile Tyr
                85                  90                  95

Glu Met Trp His Asn Tyr Pro Phe Leu Phe Gly Pro Val Gly Cys Tyr
            100                 105                 110

Phe Lys Thr Ala Leu Phe Glu Thr Val Cys Phe Ala Ser Ile Leu Ser
        115                 120                 125

Val Thr Thr Val Ser Val Glu Arg Tyr Val Ala Ile Val His Pro Phe
    130                 135                 140

Arg Ala Lys Leu Glu Ser Thr Arg Arg Ala Leu Arg Ile Leu Ser
145                 150                 155                 160

Leu Val Trp Ser Phe Ser Val Val Phe Ser Leu Pro Asn Thr Ser Ile
                165                 170                 175

His Gly Ile Lys Phe Gln His Phe Pro Asn Gly Ser Ser Val Pro Gly
            180                 185                 190
```

Ser Ala Thr Cys Thr Val Thr Lys Pro Met Trp Val Tyr Asn Leu Ile
        195                 200                 205

Ile Gln Ala Thr Ser Phe Leu Phe Tyr Ile Leu Pro Met Thr Leu Ile
        210                 215                 220

Ser Val Leu Tyr Tyr Leu Met Gly Leu Arg Leu Lys Arg Asp Glu Ser
225                 230                 235                 240

Leu Glu Ala Asn Lys Val Ala Val Asn Ile His Arg Pro Ser Arg Lys
                245                 250                 255

Ser Val Thr Lys Met Leu Phe Val Leu Val Leu Val Phe Ala Ile Cys
            260                 265                 270

Trp Thr Pro Phe His Val Asp Arg Leu Phe Phe Ser Phe Val Glu Glu
        275                 280                 285

Trp Thr Glu Ser Leu Ala Ala Val Phe Asn Leu Ile His Val Val Ser
        290                 295                 300

Gly Val Phe Phe Tyr Leu Ser Ser Ala Val Asn Pro Ile Ile Tyr Asn
305                 310                 315                 320

Leu Leu Ser Arg Arg Phe Arg Ala Ala Phe Arg Asn Val Val Ser Pro
                325                 330                 335

Thr Cys Lys Trp Cys His Pro Arg His Gln Pro Gln Gly Pro Pro Ala
            340                 345                 350

Gln Lys Ile Ile Phe Leu Thr Glu Cys His Leu Met Glu Leu Thr Glu
        355                 360                 365

Asp Ala Gly Pro Gln Phe Pro Gly Gln Ser Ser Ile His Asn Thr Asn
370                 375                 380

Leu Thr Met Ala Pro Cys Ala Gly Glu Val Pro
385                 390                 395

<210> SEQ ID NO 22
<211> LENGTH: 1185
<212> TYPE: DNA
<213> ORGANISM: Rat

<400> SEQUENCE: 22
atgggaaaac ttgaaaatgc ttcctggatc cacgatccac tcatgaagta cttgaacagc     60
acagaggagt acttggccca cctgtgtgga cccaagcgca gtgacctatc ccttccggtg    120
tctgtggcct atgcgctgat cttcctggtg ggggtaatgg gcaatcttct ggtgtgcatg    180
gtgattgtcc gacatcagac tttgaagaca cccaccaact actatctctt cagcttggca    240
gtctcagatc tgctggtcct gctcttgggg atgcctctgg aaatctacga gatgtggcac    300
aattaccctt tcctgttcgg gcctgtggga tgctacttca agacagccct cttcgagact    360
gtgtgctttg cctccattct cagtgtcacc acggttagcg tagagcgcta tgtggccatt    420
gtccacccct tccgagccaa gctggagagc acgcggcgac gggccctcag gatcctcagc    480
ctagtctgga gcttctctgt ggtcttttct tgcccaatac cagcatcca tggcatcaag    540 ttccagcact tcccaacgg tcctccgta cctggctcag ccacctgcac agtcaccaaa    600
cccatgtggg tgtataactt gatcatccaa gctaccagct tcctcttcta catcctccca    660
atgaccctca tcagcgtcct ctactacctc atggggctca ggctgaagag agatgaatcc    720
cttgaggcga acaaagtggc tgtgaatatt cacagaccct ctagaaagtc agtcaccaag    780
atgctgtttg tcttggtcct cgtgtttgcc atctgctgga ccccttcca tgtggaccgg    840 ctcttcttca gctttgtgga agagtggaca gagtccctgg ctgctgtgtt caacctcatc    900
catgtggtat caggtgtctt cttttatctg agctccgcgg tcaaccccat tatctataac    960

```
ctcctgtctc ggcgcttccg ggcggcctttt cgaaatgttg tctcccctac ctgcaaatgg    1020
tgccatcccc ggcatcagcc acagggacct ccagcccaga agatcatctt cttgacagaa    1080
tgtcacctca tggagctgac agaggatgca ggccccagt tccctggtca gtcatccatc     1140
cacaacacca accttaccat ggccccctgt gcgggagagg tacca                    1185
```

SCREENING METHOD

FIELD OF THE INVENTION

This application is the National Phase filing of International Patent Application No. PCT/JP01/00746, filed Feb. 2, 2001.

The present invention relates to a novel receptor protein TGR-1 derived from human testis and rat uterus, a DNA encoding TGR-1, and a screening method for a prophylactic and/or therapeutic agent for hypertension or stress-related diseases, or an agent for controlling appetite, which is characterized by using TGR-1 and Neuromedin U (Minamino, N. et al., Biochem. Biophys. Res. Commmun. 130, 1078–1085, 1985), or derivatives or salts thereof.

BACKGROUND ART

A variety of hormones and neurotransmitters regulate the biological functions through specific receptor proteins located in a cell membrane. Many of these receptor proteins are coupled with guanine nucleotide-binding proteins (hereinafter sometimes referred to as G proteins) and evoke the intracellular signal transduction via activation of the G proteins. These receptor proteins possess the common structure, i.e. seven transmembrane domains and are thus collectively referred to as G protein-coupled receptors or seven-transmembrane receptors (7TMR).

An important regulation of biological functions, such as homeostasis, reproduction, individual development, metabolism, growth, regulations of nervous system, respiratory system, digestive system and metabolic system, and sensory system is conducted through an interaction between these hormones or neurotransmitters and G protein-coupled receptor proteins. In this context, it is known that there are various receptor proteins for hormones and neurotransmitters for the regulation of biological functions and these proteins play an important role for regulating the functions. However, it is not much clear as to whether unknown active substances (e.g. hormones, neurotransmitters, etc.) and receptors thereof still exist.

In recent years, using the fact that G protein-coupled receptor proteins represent similarities in their partial amino acid sequences, the search for DNA encoding a novel receptor protein is conducted by Polymerase Chain Reaction (hereinafter abbreviated as PCR) method. Therefore, many orphan G protein-coupled receptor proteins whose ligand are not known, are cloned (Libert, F., et al. Science, 244, 569–572, 1989, Welch, S. K., et al., Biochem. Biophys. Res. Commun., 209, 609–613, 1995, Marchese, A., et al., Genomics, 23, 609–618, 1994, Marchese, A., Genomics, 29, 335–344, 1995). Novel G protein-coupled receptor proteins are also found by random analysis of genomic DNA or cDNA sequences (Nomura, N., et al., DNA Research vol. 1, 27–25, 1994). General methods for determining a ligand to an orphan G protein-coupled receptor protein are only to predict the ligand from similarity of the primary structure of G protein-coupled receptor protein. However, since many G protein-coupled receptor proteins represent low homology with the known receptors, it is difficult to predict a ligand only from the similarity of the primary structure unless the receptor protein is a subtype receptor for the known ligand. On the other hand, many orphan G protein-coupled receptor proteins are found by genetic analysis. So, it is estimated that there are many unknown ligands still remained. Nevertheless, only a few ligands for G protein-coupled receptor proteins are actually identified.

On the other hand, Neuromedin U is a peptide, which was isolated and purified from porcine spinal cords, with setting a rat uterus smooth muscle contraction activity as an index. Two kinds of Neuromedin U, Neuromedin U-8 having 8 amino acid residues and Neuromedin U-25 having 25 amino acid residues are first reported (Minamino, N. et al., Biochem. Biophys. Res. Commun. 130, 1078–1085, 1985). Since the sequence of Neuromedin U-8 is identical to C-terminal sequence of Neuromedin U-25 and the upstream region contains a basic amino acid pair often seen in the cleavage site for processing, both Neuromedin U are expected to be derived from a common precursor. Also, other physiological functions besides the smooth muscle contraction activity are widely known. Such functions reportedly include, for example, increase in blood pressure (Minamino. N. et al.), decrease in bloodstream of intestine (Sumi, S. et al., Life Sci. 41, 1585–1590, 1987), adjustment of ion transportation in intestine (Brown, D. R. and Quito, F. L., Eur. J. Pharmacol. 155, 159–162, 1998) and increase in ACTH and subsequent increase in corticosterone after hypodermic administration of Neuromedin U (Malendowicz, L. K. et al., In Vivo, 7, 419–422, 1993).

SUMMARY OF THE INVENTION

Until now, only FM-3 has been identified as a receptor for Neuromedin U (WO 00/02918). However, there is a need to develop a new drug by finding a receptor for Neuromedin U other than FM-3, clarifing the physiological role of Neuromedin U, and screening a compound that activates or inhibits its action.

The present inventors have found, with extensive investigation, a new orphan G protein-coupled receptor protein TGR-1, and also found unexpectedly that Neuromedin U has the cell stimulating activity to the TGR-1-expressing CHO cells in a specific manner. Based on these findings, the present inventors continued extensive studies to accomplish the present invention.

Thus, the present invention relates to the followings:

(1) A method for screening a compound or a salt thereof that alters the binding property of Neuromedin U or a salt thereof with a protein or a salt thereof comprising the same or substantially the same amino acid sequence as the sequence shown by SEQ ID NO:1 or NO:21, which is characterized by using Neuromedin U, a derivative thereof or a salt thereof and a protein or a salt thereof comprising the same or substantially the same amino acid sequence as the sequence shown by SEQ ID NO:1 or NO:21.

(2) A kit for screening a compound or a salt thereof that alters the binding property of Neuromedin U or a salt thereof with a protein or a salt thereof comprising the same or substantially the same amino acid sequence as the sequence shown by SEQ ID NO:1 or NO:21, which is characterized by comprising Neuromedin U, a derivative thereof or a salt thereof and a protein or a salt thereof comprising the same or substantially the same amino acid sequence as the sequence shown by SEQ ID NO:1 or NO:21.

(3) A compound or a salt thereof that alters the binding property of Neuromedin U or a salt thereof with a protein or a salt thereof comprising the same or substantially the same amino acid sequence as the sequence shown by SEQ ID NO:1 or NO:21, which is obtainable using the screening method described in (1) or the screening kit described in (2).

(4) A pharmaceutical composition comprising the compound described in (3).

(5) A pharmaceutical composition described in (4), which is a therapeutic and prophylactic agent for obesity, hypertension or stress-related diseases.

(6) A screening method described in (1) or a screening kit described in (2), where Neuromedin U is a peptide comprising the same or substantially the same amino acid sequence as the sequence shown by SEQ ID NO:11.

(7) A protein or a salt thereof comprising the same or substantially the same amino acid sequence as the sequence shown by SEQ ID NO:1 or NO:21.

(8) A DNA containing the DNA encoding the protein described in (7).

(9) A DNA described in (8) having the base sequence shown by SEQ ID NO:2 or No:22.

(10) A recombinant vector containing the DNA described in (8).

(11) A transformant transformed with the recombinant vector described in (10).

(12) A method for producing the protein or salt thereof described in (7), characterized by cultivating the transformant described in (11) and making the transformant produce the protein described in (7).

(13) An antibody to the protein or salt thereof described in (7).

In the present invention, Neuromedin U specifically includes the above-mentioned Neuromedin U or a salt thereof, and also:

(14) Neuromedin U includes proteins (polypeptides) comprising the amino acid sequence shown by SEQ ID NO:5, NO:6, NO:7, NO:8, NO:9, NO:10, NO:12, NO:13, NO:14 or NO:15, or derivatives or salts thereof.

For Neuromedin U of the present invention, it is preferred that the carboxyl group of the C-terminal amino acid is amidated.

TGR-1 of the present invention specifically includes the protein or a salt thereof comprising the same or substantially the same amino acid sequence as the sequence shown by SEQ ID NO:1 or NO:21, and also:

(15) TGR-1 includes the protein or a salt thereof comprising the same or substantially the same amino acid sequence as the sequence shown by SEQ ID NO:17;

(16) TGR-1 includes proteins or salts thereof comprising the amino acid sequence shown by SEQ ID NO:1, NO:17 or NO:21 wherein 1 to 30 amino acids, preferably 1 to 10 amino acids are deleted, wherein 1 to 30 amino acids, preferably 1 to 10 amino acids are added (iserted), wherein 1 to 30 amino acids, preferably 1 to 10 amino acids are substituted with other amino acids.

More specifically, TGR-1 includes proteins comprising the part from 4 (Met) through 415 (Thr) positions of the amino acid sequence shown by SEQ ID NO:1 or NO:17.

BRIEF DESCRIPTION OF THE DRAWINGS

FIG. 2 shows the comparison of human TGR-1 (Human.pro=SEQ ID NO:1) obtained in Example 1 and rat TGR-1 (rat.PRO-SEQ ID NO:21) obtained in Example 3 in terms of amino acid sequence.

BEST MODE OF THE INVENTION

Figure 1:
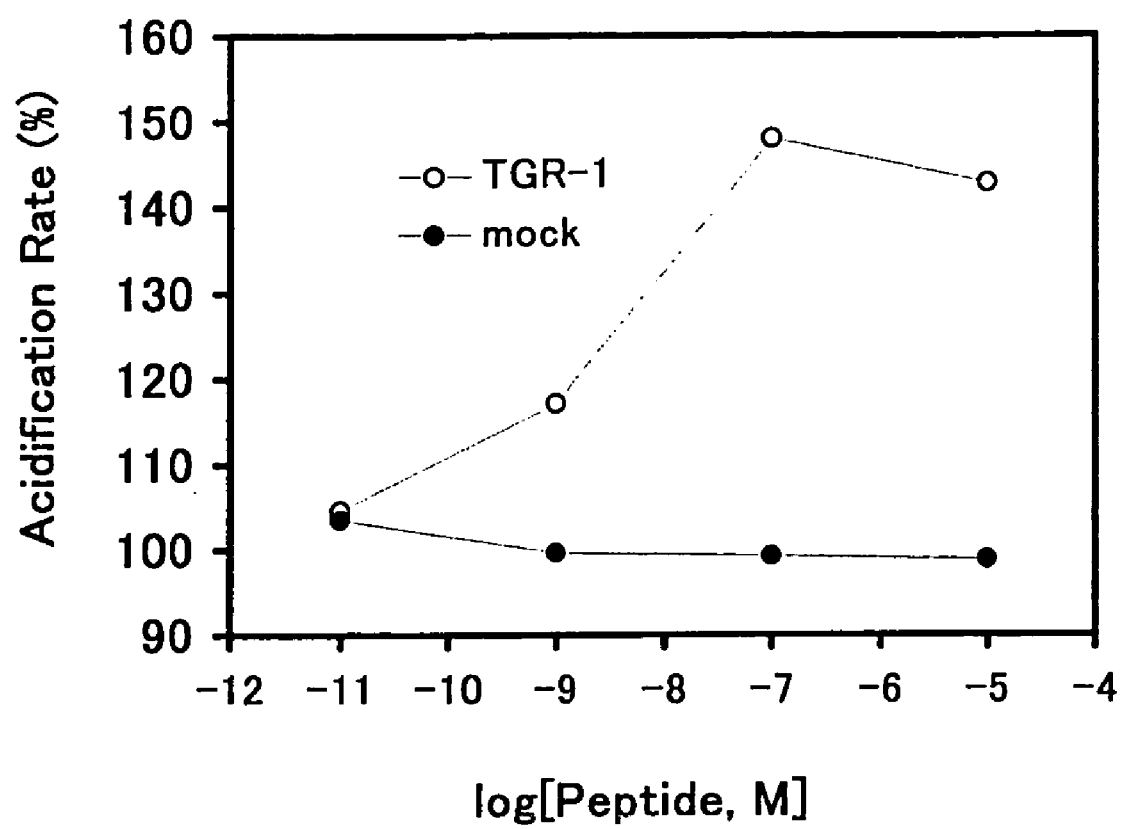
FIG. 1 shows the result of detection of TGR-1 receptor-specific cell-stimulating activity using the site sensor, performed in Example 2. In the site sensor assay, pig Neuromedin U-8 at the concentrations indicated in FIG. 1 was reacted to TGR-1-expressing CHO cells (●) and mock CHO cells (○) for 7 minutes and 2 seconds. The maximum of acidification rate during the reaction was plotted.

The details of method for producing TGR-1 or a salt thereof (hereinafter simply referred to as TGR-1) and Neuromedin U, a derivative thereof or a salt thereof (hereinafter simply referred to as Neuromedin U) are described as follows.

TGR-1 and Neuromedin U of the present invention may be any proteins ((poly)peptides) derived from any tissues (e.g. hypophysis, pancreas, brain, kidney, liver, gonad, thyroid, gallbladder, bone marrow, adrenal gland, skin, muscle, lung, gastrointestinal tract, blood vessel, heart, etc.) or any cells from warm-blooded animals (e.g. human, guinea pig, rat, mouse, swine, sheep, bovine, monkey, dog, chicken), amphibian (e.g. frog) and fish. TGR-1 may be any proteins ((poly)peptides) having the same or substantially the same amino acid sequence as that shown by SEQ ID NO:1 or NO:21, and Neuromedin U may be any proteins having the same or substantially the same amino acid sequence as that shown by SEQ ID NO:11.

TGR-1 includes a protein having the substantially same activity as that of the protein having the amino acid sequence shown by SEQ ID NO:1 or NO:21, as well as the protein containing the amino acid sequence shown by SEQ ID NO:1 or NO:21.

Herein, the term "substantially same" means the substantial equiavalence in the binding activity of a ligand (Neuromedin U) and a receptor (TGR-1), a physiological property or the like. The substitution, deletion, addition and insertion of amino acids in a plypeptide often do not give a detectable change in physiological and chemical properties of the polypeptide. In such case, the protein ((poly)peptide) that is modified by the substitution, deletion, addition or insertion (so called a variant of Neuromedin U, TGR-1, or the like) is considered to be substantially the same as the protein which is not modidifed.

The amino acid in said amino acid sequence can be substituted with substantially the same amino acid selected from, for example, other amino acids of the group that the amino acid belongs to. Non-polar (hydrophobic) amino acid includes alanine, leucine, isoleucine, valine, proline, phenylalanine, tryptophan, methionine, etc. Polar (neutral) amino acid includes glycine, serine, threonin, cycteine, thyrosine, asparagine, glutamine, etc. Positively charged (basic) amino acid includes arginine, lysine, histidine, etc. Negatively charged (acidic) amino acid includes aspartic acid, glutamic acid, etc.

Therefore, these proteins may vary in quantitative factors such as a binding activity level, a molecular weight, etc.

More specific examples of the substantially same amino acid sequence as the sequence shown by SEQ ID NO:1 or NO:21 include an amino acid sequence with at least about 90%, more preferably at least about 95%, even more preferably at least about 98% homology with the sequence shown by SEQ ID NO:1 or NO:21.

In particular, examples of the substantially same amino acid sequence as the sequence shown by SEQ ID NO:1 include an amino acid sequence which comprises the amino acid sequence of Leu-Phe-Val, Trp-Ser-Glu, Val-Phe-Phe, or Ser-Met-His as a partial sequence, and has preferably at least about 90%, more preferably at least about 95%, even more preferably at least about 98% homology with the sequence shown by SEQ ID NO:1.

Preferred examples of a protein comprising the substantially same amino acid sequence as the sequence shown by SEQ ID NO:1 or NO:21 include a protein which has the substantially same amino acid sequence as the sequence shown by SEQ ID NO:1 or NO:21, and the substantially same activity as that of the amino acid sequence shown by SEQ ID NO:1 or NO:21.

Examples of a protein comprising the substantially same amino acid sequence as the sequence shown by SEQ ID NO:1 include a proteins which comprises the amino acid sequence of Leu-Phe-Val, Trp-Ser-Glu, Val-Phe-Phe, or Ser-Met-His as a partial sequence, or preferably has the substantially same amino acid sequence as the sequence shown by SEQ ID NO:1, and the substantially same activity as that of the amino acid sequence shown by SEQ ID NO:1.

Examples of "the substantially same activity" include the ligand binding activity, the signal transducing activity, etc. The term "substantially same" means the qualitative equivalence in these activities. Thus, it is preferred that an activity, such as the ligand binding activity, the signal transducing activity, etc. is quantitatively equivalent (for example, about 0.01 to 100 times, preferably about 0.5 to 20 times, more preferably about 0.5 to 2 times), but quantitative factors, such as levels of these activity, a molecular weight, etc. may vary.

These activities, such as the ligand binding activity, the signal transducing activity can be measured according to a known method, for example, the screening method as described below.

In addition, examples of the substantially same amino acid sequence as the sequence shown by SEQ ID NO:1 or NO:21 include (i) an amino acid sequence in which one or more (preferably 1 to 30, more preferably 1 to 10, and even more preferably several (1 to 5)) amino acids are deleted from the amino acid sequence represented by SEQ ID NO:1 or NO:21; (ii) an amino acid sequence in which one or more (preferably 1 to 30, more preferably 1 to 10, and even more preferably several (1 to 5)) amino acids are added to the amino acid sequence represented by SEQ ID NO:1 or NO:21; (iii) an amino acid sequence in which one or more (preferably 1 to 30, more preferably 1 to 10, and even more preferably several (1 to 5)) amino acids are substituted with other amino acids in the amino acid sequence represented by SEQ ID NO:1 or NO:21; and (iv) an amino acid sequence comprising any combination of the above modifications.

In addition, examples of the substantially same amino acid sequence as the sequence shown by SEQ ID NO:1 include (i) an amino acid sequence in which one or more (preferably 1 to 30, more preferably 1 to 10, and even more preferably several (1 to 5)) amino acids are deleted from the amino acid sequence represented by SEQ ID No:1, and which comprises the amino acid sequence of Leu-Phe-Val, Trp-Ser-Glu, Val-Phe-Phe, or Ser-Met-His as a partial sequence; (ii) an amino acid sequence in which one or more (preferably 1 to 30, more preferably 1 to 10, and even more preferably several (1 to 5)) amino acids are added to the amino acid sequence represented by SEQ ID NO:1, and which comprises the amino acid sequence of Leu-Phe-Val, Trp-Ser-Glu, Val-Phe-Phe, or Ser-Met-His as a partial sequence; (iii) an amino acid sequence in which one or more (preferably 1 to 30, more preferably 1 to 10, and even more preferably several (1 to 5)) amino acids are substituted with other amino acids in the amino acid sequence represented by SEQ ID NO:1, and which comprises the amino acid sequence of Leu-Phe-Val, Trp-Ser-Glu, Val-Phe-Phe, or Ser-Met-His as a partial sequence; and (iv) an amino acid sequence comprising any combination of the above modifications.

Furthermore, examples of TGR-1 include a protein comprising a portion from 4th (Met) to 415th (Thr) position from the N-terminal of the amino acid sequence shown by SEQ ID NO:1 or NO:17.

On the other hand, examples of Neuromedin U of the present invention include (poly)peptides having the substantially same activity as that of the (poly)peptide having the amino acid sequence shown by SEQ ID NO:11, in addition to the (poly)peptide having the amino acid sequence shown by SEQ ID NO:11.

Examples of "the substantially same activity" include the binding activity of the receptor, and the like. The term "substantially same" means the qualitative equivalence, for example, in the binding activity of the receptor, and the like. Therefore, quantitative factors such as a binding activity level, a molecular weight, etc. may vary.

In the present specification, the amino acid sequences of TGR-1 and Neuromedin U are shown so that the N-terminal (amino terminal) is placed in the left and the C-terminal (carboxyl terminal) in the right, in accordance with a conventional peptide notation system. The protein or (poly)peptide having the amino acid sequence shown by SEQ ID NO: 1 or NO:21, or NO:11 usually has a carboxyl group (—COOH) or carboxylate (—COO$^-$) at the C-terminal, but may have an amide (—CONH$_2$) or ester (—COOR) at the C-terminal.

R in said ester includes, for example, $C_{1-6}$ alkyl groups such as methyl, ethyl, n-propyl, isopropyl and n-butyl; $C_{3-8}$ cycloalkyl groups such as cyclopentyl and cyclohexyl; $C_{6-12}$ aryl groups such as phenyl and α-naphthyl; $C_{7-14}$ aralkyl groups such as phenyl-$C_{1-2}$ alkyl, such as benzyl, phenethyl and benzhydryl, and α-naphthyl-$C_{1-2}$ alkyl, such as α-naphthylmethyl; and pivaloyloxymethyl groups generally used as an ester suitable for oral administration.

Preferred example of Neuromedin U of the present invention is the one having an amide (—CONH$_2$) at the C-terminal.

Examples of salts of TGR-1 or Neuromedin U used in the present invention include salts with physiologically acceptable bases (e.g., alkali metals) or acids (e.g., inorganic acids, organic acids). Specially, physiologically acceptable acid addition salts are preferred. Such salts include, for example, salts with inorganic acids (e.g., hydrochloric acid, phosphoric acid, hydrobromic acid, sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The TGR-1 or Neuromedin U used in the present invention can be produced by a known method (the method described in FEBS Letters, 398(1996), 253–258, or WO 96/18651). That is, it can be produced by a polypeptide purification technique from the human or warm-blooded animal cells or tissues, or can be produced according to a peptide synthesis method described below. Alternatively, it can be produced by culturing a transformant containing the DNA encoding the protein (peptide) described below.

When the protein is produced from tissues or cells of human, warm-blooded animal, amphibian or fish, the tissues or cells are homogenized, then extracted with an acid, an organic solvent or the like, and then the protein is isolated and purified from the extract by a combination of chromatography techniques such as salting out, dialysis, gel filtration, reverse-phase chromatography, ion-exchange chromatography, affinity chromatography, etc.

TGR-1 or Neuromedin U used in the present invention can be produced according to a known method for peptide synthesis or by cleaving a protein ((poly)peptide) containing TGR-1 or Neuromedin U with a suitable peptidase. For example, the protein ((poly)peptide) synthesis method may be the solid- or liquid-phase synthesis method. That is, the desired protein ((poly)peptide) can be obtained by condensation of partial peptides or amino acids composing TGR-1 or Neuromedin U with the remaining parts, followed by elimination of protecting groups, if any, from the product.

The known methods for condensation and elimination of protecting groups can be found in e.g. the following (1) to (5):
(1) M. Bodanszky and M. A. Ondetti, Peptide Synthesis, Interscience Publisher, New York (1966);
(2) Schroeder and Luebke, The Peptide, Academic Press, New York (1965);
(3) Nobuo Izumiya et al., Basis and Experiments in Peptide Synthesis, Maruzen Co., Ltd. (1975);
(4) Haruaki Yajima and Shunpei Sakakibara, Biochemical Experimental Course 1, Protein Chemistry IV, 205, (1977); and
(5) Haruaki Yajima (supervisor), Development of medicines, a second series, vol.14, Peptide Synthesis, Hirokawashoten.

After the reaction, the protein ((poly)peptide) can be isolated and purified by a combination of conventional purification techniques such as solvent extraction, distillation, column chromatography, liquid chromatography and recrystallization. If the protein ((poly)peptide) is obtained in a free form by these methods, the product can be converted into a suitable salt by a known method, or if the protein ((poly)peptide) is obtained in a salt form, it can be converted into a free form by a known method.

For synthesis of amide derivative of TGR-1 or Neuromedin U, usually commercially available resin for protein synthesis can be used. Such resin includes, for example, chloromethyl resin, hydroxymethyl resin, benzhydryl amine resin, aminomethyl resin, 4-benzyloxybenzyl alcohol resin, 4-methylbenzhydryl amine resin, PAM resin, 4-hydroxymethylmethylphenylacetamidemethyl resin, polyacrylamide resin, 4-(2',4'-dimethoxyphenyl-hydroxymethyl) phenoxy resin, 4-(2',4'-dimethoxyphenyl-Fmoc aminoethyl)phenoxy resin, and so forth. On the resin described above, each amino acid with the α-amino group and side-chain functional group properly protected is condensed sequentially in accordance with the sequence of the desired peptide by the per se known condensation methods. At the end of the reaction, the protein ((poly)peptide) is cleaved off from the resin, and various protecting groups are removed, and the product is subjected to a reaction of forming intramolecular disulfide bonds in a highly dilute solution to give the desired protein ((poly)peptide).

A wide variety of activating reagents usable for protein synthesis can be used for condensation of the protected amino acids described above, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids along with racemization inhibitors (e.g., HOBt, HOOBt) can be added to the resin directly or after the protected amino acids were previously activated as symmetric acid anhydrides or HOBt esters or HOOBt esters. The solvent used for activation of each protected amino acid or for condensation thereof with the resin can be selected as necessary from those solvents known to be usable in protein ((poly)peptide) condensation reaction. Examples of such solvent include acid amides such as N,N-dimethylformamide, N,N-dimethylacetamide and N-methylpyrrolidone; halogenated hydrocarbons such as methylene chloride and chloroform; alcohols such as trifluoroethanol; sulfoxides such as dimethyl sulfoxide; tertiary amines such as pyridine; ethers such as dioxane and tetrahydrofuran; nitrites such as acetonitrile and propionitrile; esters such as methyl acetate and ethyl acetate, or a suitable mixture thereof. The reaction temperature is usually selected as necessary within the range known to be usable in the reaction of forming peptide bonds, and usually the reaction temperature is selected within the range of about −20° C. to 50° C. The activated amino acid derivatives are used usually in excess (1.5- to 4-fold). When their condensation is insufficient as a result of a ninhydrin reaction test, their sufficient condensation is achieved by repeatedly carrying out the condensation reaction without conducting elimination of the protecting groups. When their sufficient condensation is not achieved even by repeatedly carrying out the reaction, the unreacted amino acids are acetylated with acetic anhydride or acetyl imidazole so that the subsequent reaction cannot be influenced.

The protecting groups for amino groups in amino acids as the starting materials include, for example, Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosfinothioyl, Fmoc etc.

The carboxyl group can be protected by, for example, $C_{1-6}$ alkyl, $C_{3-8}$ cycloalkyl, $C_{7-14}$ aralkyl as above described for, or 2-adamantyl, 4-nitrobenzyl, 4-methoxybenzyl, 4-chlorobenzyl, phenacyl, benzyloxycarbonylhydrazide, t-butoxycarbonylhydrazide, tritylhydrazide, etc.

The hydroxyl group in serine and threonine can be protected by, for example, esterification or etherification. A suitable group used in this esterification includes, for example, lower alkanoyl groups such as acetyl group; alloyl groups such as benzoyl group; and carbonic acid-derived groups such as benzyloxycarbonyl group and ethoxycarbonyl group. A suitable group for etherification includes, for example, a benzyl group, tetrahydropyranyl group, t-butyl group, etc.

The protecting group used for the phenolic hydroxyl group in tyrosine includes, for example, Bzl, $Cl_2$-Bzl, 2-nitrobenzyl, Br-Z, t-butyl etc.

The protecting group used for imidazole in histidine includes, for example, Tos, 4-methoxy-2,3,6-trimethylbenzenesulfonyl, DNP, benzyloxymethyl, Bum, Boc, Trt, Fmoc etc.

Activated carboxyl groups in the starting materials include, for example, the corresponding acid anhydrides, azides and active esters (i.e. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide and HOBt). The activated amino groups in the starting materials include, for example, the corresponding phosphoric acid amides.

Examples of methods for removing (leaving) of the protecting groups include catalytic reduction in a hydrogen stream in the presence of a catalyst such as Pd-black or Pd-carbon; acid treatment using anhydrous hydrogen fluoride, methane sulfonic acid, trifluoromethane sulfonic acid, trifluoroacetic acid or a mixed solution thereof; base treatment using diisopropylethylamine, triethylamine, piperidine or piperazine; and reduction using sodium in liquid ammonia. The leaving reaction by the acid treatment is carried out generally at a temperature of about −20° C. to 40° C., and it is useful in the acid treatment to add a cation scavenger such as anisole, phenol, thioanisole, m-cresol, p-cresol, dimethylsulfide, 1,4-butanedithiol and 1,2-ethanedithiol. A 2,4-dinitrophenyl group used as a protecting group for imidazole in histidine can also be removed by treatment with thiophenol, while a formyl group used as a protecting group for indole in tryptophan can be removed for deprotection by acid treatment in the presence of 1,2-ethanedithiol or 1,4-butanedithiol above, or also by alkali treatment using dilute sodium hydroxide solution or dilute ammonia.

Protection and protecting groups for functional groups which should not participate in the reaction of the starting materials, elimination of the protecting groups, and activation of functional groups participating in the reaction can be selected as necessary from known groups or known means.

Another method of obtaining an amide derivative of TGR-1 or Neuromedin U includes, for example, amidating the α-carboxyl group of a C-terminal amino acid, then extending a peptide chain at the side of the amino group until it attains desired chain length, and thereafter producing a peptide of said peptide chain from which only the protecting group for the N-terminal α-amino group was removed and a peptide of said peptide chain from which only the protecting group for the C-terminal carboxyl group was removed, followed by condensation both the proteins in the mixed solvent as described above. The details of the condensation reaction are the same as described above. The protected protein obtained by condensation is purified, and every protecting group is removed by the method descried above, whereby the desired crude protein ((poly)peptide) can be obtained. This crude protein ((poly)peptide) is purified by a wide variety of known purification techniques, and by lyophilizing its major fraction, the desired amide derivative of the protein ((poly)peptide) can be obtained.

To obtain an ester derivative of TGR-1 or Neuromedin U, for example, the α-carboxyl group of a C-terminal amino acid is condensed with desired alcohol to form an amino acid ester, from which the desired ester derivative of the protein ((poly)peptide) can be obtained in the same manner as for the amide derivative of the protein ((poly)peptide).

The Neuromedin U derivatives used in the present invention may be any having a binding activity with TGR-1, such as (1) a partial peptide of Neuromedin U; (2) a peptide wherein the constitutive amino acid of Neuromedin U was deleted, a peptide wherein other amino acids is added to the constitutive amino acid, a peptide wherein the constitutive amino acid is substituted by other amino acids; or (3) a labeled Neuromedin U, a labeled partial peptide described in (1) or a labeled peptide described in (2).

Specifically, the partial peptide of Neuromedin U includes the peptide having the amino acid sequence shown by SEQ ID NO:16, its amide derivatives, its ester derivatives or a salt thereof. Among those, the amide derivatives of the peptide having the amino acid sequence shown by SEQ ID NO:16 or its salt are preferred.

The partial peptide of Neuromedin U can be produced by cleaving Neuromedin U desclosed in the above with a suitable peptidase or according to the above-mentioned protein ((poly)peptide) synthesis method. The amide derivatives and the ester derivatives of the partial peptide of Neuromedin U can be produced according to the above-mentioned amide derivative production method or the above-mentioned ester derivative production method. Moreover, salt of the partial peptide of Neuromedin U includes the same salts as the above-mentioned salt of TGR-1 or Neuromedin U.

Examples of the Neuromedin U peptide wherein any constitutive amino acids of Neuromedin U are deleted, wherein other amino acids are added to the constitutive amino acids, or wherein any of the constitutive amino acids is substituted by other amino acids include peptides having the amino acid sequence shown by SEQ ID NO:11, wherein 1 to 3, preferably 1 or 2 amino acids are deleted, wherein 1 to 3, preferably 1 or 2 amino acids are added (or inserted), or wherein 1 to 3, preferably 1 or 2 amino acids are substituted with other amino acids.

Furthermore, examples of said peptide wherein any constitutive amino acids are deleted, peptides wherein other amino acids are added to the constitutive amino acids, peptides wherein any constitutive amino acids are substituted by other amino acids include peptides having the amino acid sequence shown by SEQ ID NO:5, NO:6, NO:7, NO:8, NO:9, NO:10, NO:12, NO:13, NO:14 or NO:15, wherein 1 to 3, preferably 1 or 2 amino acids are deleted, wherein 1 to 3, preferably 1 or 2 amino acids are added (or inserted), or wherein 1 to 3, preferably 1 or 2 amino acids are substituted with other amino acids.

The amino acid in said amino acid sequence can be substituted with substantially the same amino acid selected from, for example, other amino acids of the group that the amino acid belongs to. Non-polar (hydrophobic) amino acid includes alanine, leucine, isoleucine, valine, proline, phenylalanine, tryptophan, methionine, etc. Polar (neutral) amino acid includes glycine, serine, threonin, cycteine, thyrosine, asparagine, glutamine, etc. Positively charged (basic) amino acid includes arginine, lysine, histidine, etc. Negatively charged (acidic) amino acid includes aspartic acid, glutamic acid, etc.

Examples of the labeled Neuromedin U, the labeled partial peptide described (1) above and the labeled peptide described (2) above include those labeled with an isotope, those labeled with fluorescence (e.g. fluorescein), those biotinated, and those labeled with enzyme accoridng to a known method.

Specifically, Neuromedin U labeled with the radioisotope such as $[^{3}H]$, $[^{125}I]$, $[^{14}C]$, $[^{35}S]$ in a known manner is used. The salt of Neuromedin U derivatives is the same salt as those salts of TGR-1 or Neuromedin U mentioned above.

The DNA encoding TGR-1 used in the present invention may be any DNA encoding the protein having the same or substantially the same amino acid sequence as that shown by SEQ ID NO:1 or NO:21, and the DNA encoding Neuromedin U used in the present invention may be any DNA encoding the peptide having the same or substantially the same amino acid sequence as that shown by SEQ ID NO:11. These DNAs may be derived from any of genomic DNA, genomic DNA library, cDNA derived from the cells and tissues described above, cDNA library derived from the cells and tissues described above, and synthetic DNA. Vectors to be used for the library may be any of bacteriophage, plasmid, cosmid and phagemid. The DNA may also be directly amplified by reverse transcriptase polymerase chain reaction (RT-PCR) using the total RNA fraction prepared from the cells and tissues described above.

An example of the DNA encoding TGR-1 having the amino acid sequence shown by SEQ ID NO:1 includes the DNA having the base sequence shown by SEQ ID NO:2. An example of the DNA encoding TGR-1 having the amino acid sequence shown by SEQ ID NO:21 includes the DNA having the base sequence shown by SEQ ID NO:22. An example of the DNA encoding TGR-1 having the amino acid sequence shown by SEQ ID NO:17 includes the DNA having the base sequence shown by SEQ ID NO:18.

Further, an example of a DNA comprising the DNA encoding TGR-1 comprising a portion from 4th (Met) to 415th (Thr) position from the N-terminal of the amino acid sequence shown by SEQ ID NO:1 includes the DNA comprising a portion from 10th (A) to 1245th (C) position from the 5'-terminal of the nucleic acid sequence shown by SEQ ID NO:2, and an example of a DNA comprising the DNA encoding TGR-1 comprising a portion from 4th (Met) to 415th (Thr) position from the N-terminal of the amino acid sequence shown by SEQ ID NO:17 includes the DNA comprising a portion from 10th (A) to 1245th (C) position from the 5'-terminal of the nucleic acid sequence shown by SEQ ID NO:18.

In particular, an example of a DNA comprising the DNA encoding TGR-1 includes a DNA which comprises the nucleic acid sequence -CTGTTTGTC- (a portion from 808th to 816th position of the sequence shown by SEQ ID NO:2), -TGGAGTGAA- (a portion from 888th to 896th position of the sequence shown by SEQ ID NO:2), -GTCTTCTTC- (a portion from 940th to 948th position of the sequence shown by SEQ ID NO:2), or -TCCATGCAC- (a portion from 1159th to 1167th position of the sequence shown by SEQ ID NO:2), and preferred is a DNA comprising the nucleic acid sequence shown by SEQ ID NO:2.

Specifically, the following DNA is used: (1) DNA hybridizing under high stringent conditions with the DNA encoding the protein or (poly)peptide having the same or substantially the same amino acid sequence as that shown by SEQ ID NO:1, NO:21 or NO:11; (2) DNA which encodes the protein or (poly)peptide having the same or substantially the same amino acid sequence as that shown by SEQ ID NO:1, NO:21 or NO:11, but which does not hybridize with the DNA sequence encoding the protein or (poly)peptide having the same or substantially the same amino acid sequence shown by SEQ ID NO:1, NO:21 or NO:11, or the sequence determined in (1), due to the degeneracy of genetic code.

Hybridization can be carried out according to a known method. The high stringent conditions used herein refer to the conditions, for example, 50% formaldehyde, 4×SSPE (1×SSPE=150 mM NaCl, 10 mM NaH$_2$PO$_4$/H$_2$O, 1 mM EDTA, pH 7.4), 5× Denhardt's solution and 0.1% of SDS at a temperature of 42° C.

The DNA encoding TGR-1 or Neuromedin U used in the present invention can be produced according to a genetic engineering method described below.

For cloning the complete DNA encoding TGR-1 or Neuromedin U of the present invention, the desired DNA may be amplified by the known PCR method using synthetic DNA primers containing a part of the base sequence encoding the polypeptide of the present invention from the above-mentioned DNA library, or DNAs inserted into an appropriate vector can be selected by hybridization with a labeled DNA fragment or synthetic DNA having a part or whole of the base sequence encoding TGR-1 or Neuromedin U. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be carried out by known methods, such as the ODA-LA PCR method, the Gupped duplex method or the Kunkel method or its modification using a known kit available as Mutan™-super Express Km or Mutan™-K (both produced by Takara Shuzo Co., Ltd.).

The cloned DNA encoding TGR-1 or Neuromedin U used in the present invention can be used depending upon purpose, as it is or if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons can also be added by using an appropriate-synthetic DNA adapter.

The expression vector for TGR-1 or Neuromedin U used in the present invention can be produced, for example, by (a) excising the desired DNA fragment from the DNA encoding TGR-1 or Neuromedin U of the present invention, and then (b) ligating the DNA fragment into an appropriate expression vector downstream of a promoter.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. The promoter used in the present invention may be any promoter suitable for a host to be used for gene expression.

When the host is animal cells, SV40 promoter, a retrovirus promoter, a metallothionein promoter, a heat shock promoter, a cytomegalovirus promoter, SRα promoter, etc can be used. When the host is Escherichia bacteria, preferred are trp promoter, T7 promoter, lac promoter, recA promoter, λP$_L$ promoter, lpp promoter, etc. When the host is Bacillus bacteria, preferred are SPO1 promoter, SPO2 promoter and penP promoter, etc. When the host is yeast, preferred are PHO5 promoter, PGK promoter, GAP promoter and ADH1 promoter, GAL promoter, etc. When the host is insect cells, preferred are polyhedrin prompter and P10 promoter, etc.

In addition, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase gene (hereinafter sometimes abbreviated as dhfr) [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker in CHO (dhfr$^-$) cell, selection can also be carried out in thymidine free medium.

If necessary, a signal sequence suitable for a host is added to the N-terminal of the polypeptide or the partial peptide. Examples of the signal sequence that can be used are Pho A signal sequence, OmpA signal sequence, etc. for an Escherichia bacterium host; α-amylase signal sequence, subtilisin signal sequence, etc. for a Bacillus bacterium host; MFα signal sequence, invertase signal sequence, etc. for a yeast host; and insulin signal sequence, α-interferon signal sequence, antibody molecule signal sequence, etc. for an animal cell host.

Using the vector containing the DNA encoding TGR-1 or Neuromedin U of the present invention thus constructed, transformants can be produced.

Examples of the host which may be employed, are Escherichia bacteria, Bacillus bacteria, yeast, insect cells, insects and animal cells, etc.

Examples of the Escherichia bacteria include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the Bacillus bacteria include *Bacillus subtilis* MI114 (Gene, 24, 255 (1983)), 207–21 (Journal of Biochemistry, 95, 87 (1984)), etc.

Examples of yeast include *Saccharomyces cereviseae* AH22, AH22R⁻, NA87-11A, DKD-5D, 20B-12, etc.

Examples of insect include a larva of *Bombyx mori* (Maeda, et al., Nature, 315, 592 (1985)).

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. Examples of the Sf cell which can be used are Sf9 cells (ATCC CRL1711) and Sf21 cells (both cells are described in Vaughn, J. L. et al., In Vitro, 13, 213–217 (1977).

Examples of animal cells include monkey cells COS-7, Vero cells, Chinese hamster cells CHO (hereinafter referred to as CHO cells), dhfr gene deficient Chinese hamster cells CHO (hereinafter simply referred to as CHO (dhfr⁻) cell), mouse L cells, mouse 3T3, mouse myeloma cells, human HEK293 cells, human FL cells, 293 cells, C127 cells, BALB3T3 cells, Sp-2/O cells, etc.

Escherichia bacteria can be transformed, for example, by the method described in Proc. Natl. Acad. Sci. U.S.A., 69, 2110 (1972) or Gene, 17, 107 (1982).

Bacillus bacteria can be transformed, for example, by the method described in Molecular & General Genetics, 168, 111 (1979).

Yeast can be transformed, for example, by the method described in Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in Virology, 52, 456 (1973).

The method of introducing the expression vector into the cell includes, for example, lipofection (Felgner, P. L. et al. Proc. Natl. Acad. Sci. U.S.A., 84, 7413 (1987)), calcium phosphate method (Graham, F. L. and van der Eb, A. J. Virology, 52, 456–467 (1973)), electroporation (Nuemann, E. et al. Embo J., 1, 841–845 (1982)), etc.

Thus, the transformant transformed with the expression vector containing the DNA encoding TGR-1 or Neuromedin U can be obtained.

Furthermore, to express TGR-1 or Neuromedin U used in the present invention in a stable manner using animal cells, the animal cell clone can be selected, into the chromosome of which the introduced expression vector is incorporated. To be more specific, using the above selection marker as an index, a transformant can be selected. From these animal cells obtained by use of the selection marker, it is possible to obtain a stable animal cell strain having a highly expressed TGR-1 or Neuromedin U used in the present invention by repeating the clonal selection. Moreover, when using dhfr gene as a selection marker, the cells are cultured in gradually increased concentrations of MTX, and the resistant cell strain is selected. In this way, it is possible to obtain the highly expression animal cell strain by amplifying the DNA encoding TGR-1 or Neuromedin U as well as dhfr gene in the cell.

TGR-1 or Neuromedin U used in the present invention can be produced by cultivating the above-mentioned transformant under condition capable of expressing the DNA encoding TGR-1 or Neuromedin U used in the present invention; and producing and accumulating TGR-1 or Neuromedin U used in the present invention.

When the host is Escherichia or Bacillus bacteria, the transformant can be appropriately cultured in a liquid medium, which contains materials required for growth of the transformant, such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may be added to the medium. Preferably, pH of the medium is about 5 to 8.

A preferred example of the medium for culturing Escherichia bacteria is M9 medium supplemented with glucose and Casamino acids (Miller, Journal of Experiments in Molecular Genetics, 431–433, Cold Spring Harbor Laboratory, New York, 1972). If necessary, a chemical such as 3β-indolylacrylic acid can be added to the medium to work the promoter efficiently.

When the host is Escherichia bacteria, the transformant is usually cultivated at about 15° C. to 43° C. for about 3 to 24 hours. If necessary, the culture may be aerated or agitated.

When the host is Bacillus bacteria, the transformant is cultivated generally at about 30° C. to 40° C. for about 6 to 24 hours. If necessary, the culture can be aerated or agitated.

When the host is yeast, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is about 5 to 8. In general, the transformant is cultivated at about 20° C. to 35° C. for about 24 to 72 hours. If necessary, the culture can be aerated or agitated.

When the host is insect cells or insects, the transformant is cultivated in, for example, Grace's Insect Medium (Grace, T. C. C., Nature, 195, 788 (1962)) to which an appropriate additive such as 10% inactivated bovine serum is added. Preferably, pH of the medium is about 6.2 to 6.4. Normally, the transformant is cultivated at about 27° C. for about 3 to 5 days and, if necessary, the culture can be aerated or agitated.

When the host is animal cells, the transformant is cultivated in, for example, MEM medium (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), which contain about 5% to about 20% fetal bovine serum. Preferably, pH of the medium is about 6 to 8. The transformant is usually cultivated at about 30° C. to 40° C. for about 15 to 60 hours and, if necessary, the culture can be aerated or agitated.

When using CHO (dhfr⁻) cells and dhfr gene as a selection marker, thymidine-free DMEM medium containing dialyzed fetal bovine serum is preferred.

TGR-1 or Neuromedin U used in the present invention can be separated and purified from the culture described above by the following procedures.

When TGR-1 or Neuromedin U used in the present invention is extracted from the cultured transformants or cells, after cultivation, the transformants or cells are collected by a well-known method, suspended in a appropriate buffer, and then disrupted by publicly known methods such as ultrasonication, a treatment with lysozyme and/or freezethaw cycling. Then by centrifugation, filtration, etc., the crude extract of TGR-1 or Neuromedin U used in the present invention can be obtained. The buffer for the extraction may contain a protein denaturizing agent, such as urea or guanidine hydrochloride, or a surfactant, such as Triton X-100™, etc.

When TGR-1 or Neuromedin U used in the present invention is secreted to the culture medium, after the cultivation, the transformants or cells can be separated to collect the supernatant by a well-known method.

TGR-1 or Neuromedin U present in the supernatant or the extract thus obtained can be purified by an appropriate combination of well-known methods for separation and purification. Such publicly known methods for separation and purification include a method utilizing difference in solubility such as salting out, solvent precipitation, etc.; a method utilizing difference mainly in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing, chromatofocusing; and the like.

When TGR-1 or Neuromedin U used in the present invention is obtained in a free form, it can be converted into a salt form by well-known methods or modifications thereof. On the other hand, when TGR-1 or Neuromedin U is obtained in a salt form, it can be converted into the free form or another salt form by well-known methods or modifications thereof.

TGR-1 or Neuromedin U used in the present invention produced by a recombinant can be treated, before or after the purification, with an appropriate protein modifying enzyme so that TGR-1 or Neuromedin U can be appropriately modified or be deprived of a partial (poly)peptide. Examples of the protein-modifying enzyme include trypsin, chymotrypsin, arginyl endopeptidase, protein kinase, glycosidase or the like. It is possible to use the well-known Edman method using Edman reagent (phenyl iso-thiocyanate) to delete the N-terminal amino acid.

The presence of the thus produced TGR-1 or Neuromedin U used in the present invention can be determined by an enzyme immunoassay using an antibody specific thereto, or the like.

The screening method for a compound or its salt that alters the binding property between Neuromedin U and TGR-1, characterized by using Neuromedin U and TGR-1, and the screening kit for a compound or its salt that alters the binding property between Neuromedin U and TGR-1, characterized by comprising Neuromedin U and TGR-1, are described in detail below.

Using the binding assay system (ligand/receptor assay system) of Neuromedin U with TGR-1 or the constructed recombinant TGR-1 expression system, the compound that alters the binding property between Neuromedin U and TGR-1 (e.g., peptides, proteins, non-peptide compounds, synthetic compounds, fermentation products, etc.) or its salt can be screened.

These compounds include the compound (TGR-1 agonist) having TGR-1-mediated cell-stimulating activities (e.g., activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation and pH change), and the compound (TGR-1 antagonist) having no such cell-stimulating activities.

The wording "alter the binding property between Neuromedin U and TGR-1" means either of properties of inhibiting or enhancing the binding between Neuromedin U and TGR-1 (prolonging the binding time).

Thus, the present invention provides: a method for screening a compound or a salt thereof that alters the binding property of Neuromedin U with TGR-1, characterized by comparing (i) a case where Neuromedin U is brought in contact with the above-mentioned TGR-1 and (ii) a case where Neuromedin U and a test compound are brought in contact with the TGR-1.

In the screening method of the present invention, for example, a binding amount of the ligand with the TGR-1 and a level of cell-stimulating activity (e.g., activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation and pH change) are measured and compared (i) where Neuromedin U is brought in contact with the above-mentioned TGR-1 and (ii) where Neuromedin U and a test compound are brought in contact with the TGR-1.

Specifically, the screening method of the present invention is:

(1) A method for screening a compound or a salt thereof that alters the binding property between Neuromedin U and TGR-1, which comprises measuring and comparing the binding amounts of a labeled Neuromedin U as one of the above-mentioned Neuromedin derivatives (hereinafter simply referred to as "labeled Neuromedin U") with the above-mentioned TGR-1, where a labeled Neuromedin U is brought in contact with the TGR-1 and where a labeled Neuromedin U and a test compound are brought in contact with the TGR-1;

(2) A method for screening a compound or a salt thereof that alters the binding property between Neuromedin U and TGR-1, which comprises measuring and comparing the binding amounts of a labeled Neuromedin U with a cell containing TGR-1 or a membrane fraction of the cell, where a labeled Neuromedin U is brought in contact with the cell or membrane fraction thereof and where a labeled Neuromedin U and a test compound are brought in contact with the cell containing TGR-1 or membrane fraction thereof;

(3) A method for screening a compound or a salt thereof that alters the binding property between Neuromedin U and TGR-1, which comprises measuring and comparing the binding amounts of a labeled Neuromedin U with TGR-1, where a labeled Neuromedin U is brought in contact with TGR-1 expressed on cell membrane of a cultured transformant containing DNA encoding TGR-1 and where a labeled Neuromedin U and a test compound are brought in contact with TGR-1 expressed on cell membrane of a cultured transformant containing DNA encoding TGR-1;

(4) A method for screening a compound or a salt thereof that alters the binding property between Neuromedin U and TGR-1, which comprises measuring and comparing TGR-1-mediated cell-stimulating activities (e.g., activities of enhancing arachidonic acid release, acetylcholine release, intracellular $Ca^{2+}$ release, intracellular cAMP production, intracellular cGMP production, inositol phosphate production, change in cell membrane potential, phosphorylation of intracellular proteins, c-fos activation and pH change), where a compound which activates TGR-1 (e.g. Neuromedin U) is brought in contact with a cell containing TGR-1 and where a compound which activates TGR-1 and a test compound are brought in contact with the cell; and (5) A method for screening a compound that or a salt thereof alters the binding property between Neuromedin U and TGR-1, which comprises measuring and comparing TGR-1-mediated cell-stimulating activities (e.g., activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation and pH change), where a compound which activates TGR-1 (e.g. Neuromedin U) is brought in contact with TGR-1 expressed on cell membrane of a cultured transformant containing DNA encoding TGR-1 and where a compound which activates TGR-1 and a test compound are brought in contact with TGR-1 expressed on the cell membrane of cultured transformant containing DNA encoding TGR-1.

Neuromedin U used in the present invention is known to have a ligand activity to an orphan receptor FM-3 (Tan, C. P. et al., Genomics 52, 223–229, 1998)(WO 00/02919). Therefore, it is possible to screen a compound which alters the binding property between Neuromedin U and FM-3 (FM-3 antagonist, FM-3 agonist) using FM-3 in place of TGR-1 in the above mehtods (1)–(5).

Accordingly, by comparing an activity of TGR-1 antagonist or TGR-1 agonist which is obtained by the screening method of the present invention, with an activity of FM-3 antagonist or FM-3 agonist which is obtained by the screening method of the present invention using FM-3 in place of TGR-1, an antagonist or agonist which acts on FM-3 preferentially over TGR-1 or which acts on TGR-1 preferentially over FM-3, can be obtained.

The term "an antagonist which acts on FM-3 preferentially over TGR-1" refers to a compound or a salt thereof in which FM-3-mediated cell-stimulating activities (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, and pH change) are at least 2 times, preferably at least 10 times weaker than TGR-1-mediated activities (receptor (TGR-1, FM-3)).

The term "an agonist which acts on FM-3 preferentially over TGR-1" refers to a compound or a salt thereof in which FM-3-mediated cell-stimulating activities (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, and pH change) are at least 2 times, preferably at least 10 times stronger than TGR-1-mediated activities (receptor (TGR-1, FM-3)).

The term "an antagonist which acts on TGR-1 preferentially over FM-3" refers to a compound or a salt thereof in which TGR-1-mediated cell-stimulating activities (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, and pH change) are at least 2 times, preferably at least 10 times weaker than FM-3-mediated activities (receptor (TGR-1, FM-3)).

The term "an agonist which acts on TGR-1 preferentially over FM-3" refers to a compound or a salt thereof in which TGR-1-mediated cell-stimulating activities (e.g. activities of enhancing arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, and pH change) are at least 2 times, preferably at least 10 times stronger than FM-3-mediated activities (receptor (TGR-1, FM-3)).

The concrete description of the screening methods of the present invention is as follows.

For the TGR-1 used in the screening method of the present invention, any substance may be used so long as it contains the above-mentioned TGR-1. The cell membrane fraction from organs of human, warm-blooded animal, amphibian or fish is preferred. Because organs, in particular human organs, are very difficult to obtain, it is preferable to use TGR-1 produced by a recombinant in a large scale. To produce TGR-1, the above-mentioned methods may be applied.

In the screening methods, the cell containing TGR-1 or the cell membrane fraction can be prepared according to the preparation method described below.

When the cells containing TGR-1 are used, the cells may be fixed using glutaraldehyde, formalin, etc. The fixation can be made by a well-known method.

The cells containing TGR-1 include host cells that have expressed TGR-1. Such host cells include *Escherichia coli*, *Bacillus subtilis*, yeast, insect cells, animal cells, and the like, as described above.

The cell membrane fraction refers to a fraction abundant in cell membrane, obtained by cell disruption and subsequent fractionation by a well-known method. The cell disruption methods include cell squashing using a Potter-Elvehjem homogenizer, disruption using a Waring blender or Polytron (produced by Kinematica Inc.), disruption by ultrasonication, and disruption by cell spraying through thin nozzles under an increased pressure using a French press or the like. Cell membrane fractionation is carried out mainly by fractionation using a centrifugal force, such as centrifugal fractionation or density gradient centrifugation. For example, after the disrupted cell solution is centrifuged at a low speed (500 rpm to 3,000 rpm) for a short period (normally about 1 to 10 minutes), the resulting supernatant is centrifuged at a higher speed (15,000 rpm to 30,000 rpm) normally for 30 minutes to 2 hours. The precipitate thus obtained is used as the membrane fraction. The membrane fraction is rich in expressed TGR-1, and membrane components, such as cell-derived phospholipids and membrane proteins.

The amount of TGR-1 in the cell containing TGR-1 and in the membrane fraction is preferably $10^3$ to $10^8$ molecules per cell, more preferably $10^5$ to $10^7$ molecules per cell. As the amount of expressed TGR-1 increases, the ligand binding activity per unit of membrane fraction (specific activity) increases so that not only the highly sensitive screening system can be constructed but also large quantities of samples can be assayed with the same lot.

To perform the methods (1) through (3) described above for screening a compound that alters the binding property between Neuromedin U and TGR-1, an appropriate TGR-1 fraction, a labeled ligand or a compound having a ligand activity (e.g. Neuromedin U and a salt thereof) are used. TGR-1 fraction is preferably a fraction of a naturally occurring receptor protein or a recombinant receptor protein having an activity equivalent to that of the natural protein.

Herein, the equivalent activity is intended to mean a ligand binding activity. For the labeled ligand and the compound having a ligand activity (e.g. Neuromedin U and a derivative thereof), for example, a ligand labeled with [$^3$H], [$^{125}$I], [$^{14}$C], [$^{35}$S], etc. (a labeled Neuromedin U as a Neuromedin U derivative) are used.

More specifically, to perform the screening for a compound that alters the binding property between Neuromedin U and TGR-1, first, a receptor preparation is prepared by suspending cells containing TGR-1 or the membrane fraction thereof in a buffer appropriate for the screening method. Any buffer can be used so long as it does not inhibit the ligand-receptor binding, such buffers including a phosphate buffer or a Tris-HCl buffer having pH of 4 to 10 (preferably pH of 6 to 8). For the purpose of minimizing non-specific binding, a surfactant such as CHAPS, Tween-80™ (Kao-Atlas Inc.), digitonin or deoxycholate, may optionally be added to the buffer. Further for the purpose of suppressing the degradation of TGR-1 and Neuromedin U by proteases, a protease inhibitor such as PMSF, leupeptin, E-64 (Peptide Institute, Inc.) and pepstatin may also be added. A given amount (5,000 to 500,000 cpm) of labeled Neuromedin U (a Neuromedin U derivative) is added to 0.01 ml to 10 ml of the receptor solution. Also, $10^{-4}$ to $10^{-1}$ iM of the test compound are added to the mixture. To determine the amount of non-specific binding (NSB), a reaction tube containing an excessive amount of unlabeled Neuromedin U is also prepared. The reaction is carried out at approximately 0 to 50° C., preferably 4 to 37° C. for 20 minutes to 24 hours, preferably 30 minutes to 3 hours. After completion of the reaction, the reaction mixture is filtrated through glass fiber filter paper, etc. and washed with an appropriate volume of the buffer. The residual radioactivity on the glass fiber filter paper is then measured with a liquid scintillation counter or γ-counter. Where regarding the count obtained by subtracting the amount of non-specific binding (NSB) from the count obtained in the absence of any competitive substance ($B_0$) as 100%, the test compound which makes the specific binding amount (B-NSB), for example 80% or less, can be selected as the compound capable of altering the binding property between TGR-1 and Neuromedin U.

For measuring the binding between TGR-1 and Neuromedin U, BIAcore (Amasham pharmacia Biotech) may be used. In this method, Neuromedin U is fixed to a sensor chip according to amino coupling method described in the protocol that is attached to the device. A buffer (such as phosphate buffer and Tris buffer) solution containing TGR-1 purified from the cells having TGR-1 or a transformant having the DNA encoding TGR-1, or a membrane fraction having TGR-1, or a buffer solution containing a purified TGR-1 or a membrane fraction having TGR-1 and a test compound is flowed on the top of the sensor chip at 2–20 μl/min. By investigating whether the co-existing test compound can alter the surface plasmo resonance change which is induced by binding TGR-1 to Neuromedin U on the sensor chip, the compound that alters the binding property between TGR-1 and Neuromedin U can be screened. This method can also be carried out by fixing TGR-1 to the sensor chip and flowing the buffer solution (such as phosphate buffer or Tris buffer) containing Neuromedin U and a test compound on the top of the sensor chip. These test compounds are as described above.

To perform the above screening methods (4) and (5) for the compound that alters the binding property between Neuromedin U and TGR-1, TGR-1-mediated cell-stimulating activity (e.g., activities of promoting or inhibiting arachidonic acid release, acetylcholine release, intracellular $Ca^{2+}$ release, intracellular cAMP production, intracellular cGMP production, inositol phosphate production, cell membrane potential change, phosphorylation of intracellular proteins, c-fos activation, pH change, etc.) can be measured using known methods or commercially available measuring kits. Specifically, the cells containing TGR-1 are first cultured on a multi-well plate. For the screening, the medium is replaced with fresh medium or with an appropriate non-cytotoxic buffer, followed by incubation for a given period of time in the presence of a test compound. Subsequently, the resulting product is quantified by appropriate procedures in the cell extract or the supernatant. When it is difficult to detect the production of the index substance (e.g., arachidonic acid) for the cell-stimulating activity, due to a degrading enzyme present in the cells, an inhibitor against such a degrading enzyme may be added before the assay. For detecting an inhibitory activity, such as the inhibition of cAMP production, the basic production in the cells can be increased by forskolin or the like and then the inhibitory effect on the increased basic production can be detected.

The screening by assay of the cell-stimulating activity requires an appropriate cell expressing TGR-1. For the cell expressing TGR-1, the recombinant cell expressing the TGR-1 described above and the like are desirable. The transformed cells capable of expressing TGR-1 can be either a stable expression strain or a transient expression strain. The same kinds of animal cells described above are used.

For the test compound, for example, peptides, proteins, non-peptide compounds, synthetic compounds, fermentation products, cell extracts, plant extracts, and animal tissue extracts are used.

To describe the above-mentioned ligand/receptor assay more specifically, the following assay systems and the like are used.

[1] When a receptor-expressing cell is stimulated by a receptor agonist, an intracellular G-protein becomes active and, as a result, GTP bonds with it. The same phenomena can be observed with a cell membrane of receptor expression cell. Generally, GTP is converted to GDP by hydrolysis. When GTPγS is added to the reaction solution, GTPγS bonds with G-protein as GTP does, and it does not suffer from hydrolysis with keeping the binding to the cell membrane containing the G-protein. Using the labeled GTPγs, it is possible to measure the receptor expression cell stimulating activity of the receptor agonist by measuring the radioactivity remaining in the cell membrane. Applying this reaction, a stimulating activity of Neuromedin U with respect to TGR-1-expressing cells can be measured. This method does not use the cells containing TGR-1 as described above (4)–(5). This method is an assay using the cell membrane containing TGR-1 as described in (1)–(3), and is an assay to measure a cell stimulating activity as described in (4)–(5). In this assay, a substance which shows an activity to promote the binding of GTPγ S to TGR-1-containing cell membrane fraction is an agonist. By adding Neuromedin U or Neuromedin U and a test compound and observing the change in GTPγS binding acceleration activity to a TGR-1-containing cell membrane fraction as compared with a single administration of Neuromedin U, the compound that alters the binding property between Neuromedin U and TGR-1 can be screened. The compound which indicates the activity that inhibits the GTPγS binding acceleration activity to a TGR-1-containing cell membrane fraction by Neuromedin U can be selected as a candidate substance which is capable of altering the binding property between TGR-1 and Neuromedin U. On the other hand, an agonist can be screened by adding a test compound alone and observing the GTPγS binding acceleration activity to a TGR-1-containing cell membrane fraction as well.

Concretely, an example of the screening methods is described as follows. A cell membrane fraction containing TGR-1 prepared by the method described above is diluted with a membrane dilution buffer solution (e.g. 50 mM Tris, 5 mM $MgCl_2$, 150 mM NaCl, 1μ GDP, 0.1% BSA pH 7.4). The dilution scale may vary according to the amount of receptor expression. 0.2 ml of the solution is transferred to Falconb 2053. Neuromedin U or Neuromedin U and a test compound are added thereto, and then [$^{35}$S]GTPγS is added to make the final concentration of 200 pM. After the mixture is kept at 25° C. for an hour, an ice-cold buffer solution for washing (50 mM Tris, 5 mM $MgCl_2$, 150 mM NaCl, 0.1% BSA, 0.05% CHAPS pH7.4 1.5 ml) is added. Then, the solution is filtered with a glass fiber filtering paper GF/F. After drying the filtering paper at 65° C. for 30 min., the radioactivity of [$^{35}$S]GTPγS bound with the membrane fraction left on the filtering paper is measured on a liquid scintillation counter. The radioactivity in the experiment with a single administration of Neuromedin U is set as 100%, the radioactivity in the experiment without adding Neuromedin U is set as 0%, and an influence of a test compound to the GTPγS binding acceleration activity by Neuromedin U is calculated. A test compound which makes GTPγS binding acceleration activity, for example 80% or less, can be selected as a candidate substance which is capable of altering the binding property between TGR-1 and Neuromedin U.

[2] When the amount of intracellular cAMP is reduced by the Neuromedin U stimulation in a TGR-1-expressing cell, using this reaction, the cell stimulating activities of Neuromedin to a TGR-1-expressing cell can be measured. Using the anti-cAMP antibody obtained by immunized mice, rats, rabbits, goats and cows and $^{125}$I-labeled cAMP (both are commercially available), the amount of cAMP production in various animal cells expressing TGR-1 can be measured by RIA or other EIA system such as the combination of anti-cAMP antibody and the labeled cAMP. It is also possible to conduct a quantification by the SPA method using beads containing the scintillant to which an anti-cAMP is fixed using Protein A or an antibody to IgG of an animal used for production of the anti-cAMP antibody, and $^{125}$I-labeled cAMP (using the kit produced by Amasham pharmacia Biotech).

In this assay system, it is possible to conduct a screening of the compound that alters the binding property of Neuromedin U and TGR-1 by increasing the amount of intracellular cAMP by ligand such as Calcitonin and Forskolin which increase the amount of intracellular cAMP; adding Neuromedin U or Neuromedin U and the test compound; and observing the change in the amount of intracellular cAMP as compared to the case with a single administration of Neuromedin U. Then, a compound that shows an inhibitory activity on the cAMP production inhibition induced by Neuromedin U in the TGR-1-expressing cells can be selected as a candidate substance that is capable of altering the binding property between TGR-1 and Neuromedin U. On the other hand, the compound that indicates an agonist activity can be screened by adding the test compound alone and measuring the cAMP production inhibition activity.

More specifically, the screening methods are described as follows. TGR-1-expressing CHO cells are plated at 5×10$^4$ cell/well on a 24-well plate, and cultivated for about 48 hours. The cells are washed with Hanks' buffer containing 0.2 mM 3-isobutylmethylxanthine, 0.05% BSA and 20 mM HEPES (pH7.4)(hereinafter referred to as reaction buffer). Then, 0.5 ml of the reaction buffer is added to the cells, and the cells are kept in an incubator for 30 minutes. Then, the reaction buffer is removed and 0.25 ml of fresh reaction buffer is added to the cells. Then, the reaction buffer (0.25 ml) containing 2 μM Forskolin in addition to 1 nM of Neuromedin U or Neuromedin U and a test compound is added to the cells. The reaction is made at 37° C. for 24 minutes. 100 μl of 20% Perchloric acid is added to stop the reaction. Then, by placing it on ice, the intracellular cAMP is extracted. The amount of cAMP in the extraction is measured by using cAMP EIA kit (Amasham pharmacia biotech). The amount of cAMP produced by the Forskolin stimulation is set as 100%, the amount of cAMP inhibited by the addition of 1 nM of Neuromedin is set as 0% and an influence of the test compound on the cAMP production inhibition activity by Neuromedin U is calculated. A test compound which makes the cAMP production activity, for example, 80% or less by inhibiting the Neuromedin U activity can be selected as a candidate substance that is capable of altering the binding property between TGR-1 and Neuromedin U.

To measure the cAMP production acceleration activity, the cAMP produced by adding a test compound to the TGR-1-expressing CHO cells without added Forskolin is measured according to the above-mentioned method. In this case, a test compound which makes the cAMP production activity, for example, 10% or more, can be selected as a candidate substance that is capable of altering the binding property between TGR-1 and Neuromedin U.

[3] The DNA containing CRE (cAMP response element) is inserted into the multi-cloning site upstream of luciferase gene of Picagene basic vector or Picagene enhancer vector (Toyo Ink). It is named as CRE-reporter gene vector. In the cell transfected with the CRE-reporter gene vector, a stimulation which causes the increase in cAMP, induces an expression of luciferase gene through CRE and a production of luciferase protein. By measuring the luciferase activity, it is possible to detect the change in the amount of cAMP in the cells into which the CRE-reporter gene vector is introduced. Thus, the compound that alters the binding property of Neuromedin U and TGR-1 can be screened using the TGR-1-expressing cells to which the CRE-reporter gene vector is transfected. The details of the screening method are as follows.

CRE-reporter gene introduced TGR-1-expressing cells is placed in a 24-well plate at a concentration of 5×10$^3$ cell/well, and cultivated for about 48 hours. The cells are washed with Hanks' buffer (pH7.4) containing 0.2 mM 3-isobutyl-methyl xanthine, 0.05% BSA and 20 mM HEPES (hereinafter, Hanks' buffer (pH7.4) containing 0.2 mM 3-isobutyl-methyl xanthine, 0.05% BSA and 20 mM HEPES, is referred to as reaction buffer) 0.5 ml of the reaction buffer is added to the cells. Then, the cells are kept warm in a cultivator for 30 minutes. Then, the reaction buffer is removed from the system. 0.25 ml of fresh reaction buffer is added to the cells. Then, the reaction buffer 0.25 ml containing 2 μ M Forskolin in addition to 1 nM of Neuromedin U or Neuromedin U and a test compound is added to the cells. The reaction is made at 37° C. for 24 minutes. The cells are dissolved in a decomposition solution for Picagene (Toyo Ink). To the decomposition solution, a luminescent substance (Toyo Ink) is added. The luminescence by luciferases is measured with a luminometer, a liquid scintillation counter, a top counter or the like. An influence of the compound that alters the binding property of Neuromedin U and TGR-1 can be measured by comparing the luminescence by luciferases with the case where Neuromedin U is singly administrated. In this process, by administrating Neuromedin U, the increase of luminescence by the Folskolin stimulation is inhibited. The compound that recovers the influence of Neuromedin U, may be selected as a candidate substance that alters the binding property between Neuromedin U and TGR-1. On the other hand, an agonist can be screened by adding the test compound singly and observing the inhibition of the increase in luminescence caused by the Folskolin stimulation, as Neuromedin U inhibits the increase.

Alkaline phosphatase, chloramphenicol, acetyltransferase or β-galactosidase can be used as a reporter gene, besides luciferase. The activity of the product of reporter gene can be measured easily using commercially available measuring kit. The activity of alkaline phosphatase can be measured by Lumi-Phos 530 (Wako); the activity of Chloramphenicol and acetyltransferase can be measured by FAST CAT chrolamphenicol Acetyltransferase Assay Kit (Wako); and the activity of β-galactosidase can be measured by Aurora Gal-XE (Wako).

[4] When TGR-1-expressing cells release the metabolic substance of arachidonic acid to the outside by the Neuromedin stimulation, if arachidonic acid having radioactivity is taken into the cell beforehand, it is possible to measure a cell stimulating activity by measuring the radioactivity released out of the cells. In this process, by adding Neuromedin U or Neuromedin U and a test compound and examining an influence of Neuromedin U on the arachidonic acid metabolite release activity, the compound that alters the binding property between Neuromedin U and TGR-1 can be screened. The compound that inhibits the arachidonic acid metabolite release activity of Neuromedin U can be selected as a candidate substance that alters the binding property of Neuromedin U and TGR-1. Moreover, the compound that indicates an agonist activity can be screened by adding the test compound singly and checking the arachidonic acid metabolite release activity in TGR-1-expressing cells.

The details of the screening method of the compound that has the influence on the binding between Neuromedin U and TGR-1 are as follows.

TGR-1-expressing CHO cells are placed at $5\times10^4$ cell/well on a 24-well plate, and cultivated for about 24 hours. After cultivation, 0.25 μCi/well of [$^3$H] arachidonic acid is added. 16 hours after adding [$^3$H] arachidonic acid, the cells are washed with Hanks' buffer (pH7.4) containing 0.05% BSA and 20 mM HEPES. Then, 500 μl of the Hanks' buffer (pH7.4) containing 0.05% BSA and 20 mM HEPES in the presence of the final concentration of 10 nM Neuromedin U or 10 nM Neuromedin U and the test compound is added to each well (hereinafter, Hanks' buffer (pH7.4) containing 0.05% BSA and 20 mM HEPES is referred to as reaction buffer). After incubating at 37° C. for 60 minutes, 400 μl of the reaction solution is added to a scintillator. Then, the amount of released [H$^3$] arachidonic acid metabolite is measured by a scintilation counter. The amount of [H$^3$] arachidonic acid metabolite in the medium without added Neuromedin U, is set as 0%, the amount of [H$^3$] arachidonic acid metabolite in the medium with added 10 nM Neuromedin, is set as 100%, and an influence of the test compound on the binding of Neuromedin U and TGR-1 is calculated. A test compound which makes the arachidonic acid metabolite production activity, for example, 50% or less, can be selected as a candidate substance that is capable of altering the binding property between TGR-1 and Neuromedin U.

[5] When Neuromedin U stimulates the increase in intracellular $Ca^{2+}$ concentration in TGR-1-expressing cells, using this fact, an influence of test compound on the binding between Neuromedin U and TGR-1 can be examined.

TGR-1-expressing cells are placed on a sterilized cover glass for a microscope. After 2 days, the medium is replaced with HBSS in which 4 mM of Fura-2 AM (Dojin Kagaku) is suspended, and left for 2 and half hours at room temperature. After washing with HBSS, the cover glass is set to a cuvet. The increase in the ratio of intensity of fluorescence at 505 nm where the excited wave length is 340 nm and 380 nm, is measured by a spectrophotofluorometer when Neuromedin U or Neuromedin U and a test compound are added. By measuring the change in the intensity of fluorescence caused by adding the test compound compared with that by the single administration of Neuromedin U, the compound which has the influence on the binding between Neuromedin U and TGR-1 can be screened. Furthermore, FLIPR (Produced by Molecular device) can be also used as follows. Fluo-3 AM (Produced by Dojin Kagaku) is added to the cell suspension to let the cells take up Fluo-3AM. The cells are washed by centrifuging several times, and placed on a 96-well plate. The cells are set to a FLIPR device, and Neuromedin U or Neuromedin U and a test compound are added in the same way as Fura-2AM. By measuring the change in the intensity of fluorescence caused by added the test compound as compared with that by the single administration of Neuromedin U, the compound which has an influence on the binding between Neuromedin U and TGR-1 can be screened. Above these, the compound that inhibits the increase in the intensity of fluorescence by Neuromedin U can be selected as a candidate substance that is capable of altering the binding property between TGR-1 and Neuromedin U. On the other hand, by observing the increase in the intensity of fluorescence by single administration of the test compound, an agonist can be screened.

To screen the compound that has an influence on the binding between Neuromedin U and TGR-1, first, TGR-1-expressing cells are allowed to co-express a gene of a protein such as Aequorin which radiates light when the intracellular Ca ion increases. The increase in the intracellular Ca ion causes Aequorin to become Ca binding type and radiates light. Using this fact, Neuromedin U or Neuromedin U and a test compound are added and the change in the intensity of luminescence when the test compound is added as compared with that by a single administration of Neuromedin U is observed for the screening. The method is almost the same as the above-mentioned method except that this method does not require cells to take up a fluorescence substance.

[6] By adding an agonist to receptor-expressing cells, the concentration of inositol triphosphate rises. By observing the reaction in TGR-1-expressing cells caused by Neuromedin U, the compound that has an influence on the binding between Neuromedin U and TGR-1 can be screened. Cells are placed in a 24-well plate, and incubated for one day, and incubated for one more day in a medium to which myo-[2-$^3$H]inositol (2.5 μ Ci/well) is added. After washing well, Neuromedin U or Neuromedin U and a test compound are added thereto, and then 10% Perchloric acid is added to stop the reaction. The reaction solution is neutralized with 1.5M KOH and 60 mM HEPES solution, and passed through a column filled with AG1x8 resin (Bio Rad). After washing with 5 mM $Na_2BO_3$ and 60 mM $HCOONH_4$, the radioactivity, which is eluted by 1M $HCOONH_4$ and 0.1M HCOOH, is measured by a liquid scintillation counter. The radioactivity in the medium when Neuromedin U is not added, is set as 0%, the radioactivity in the medium when Neuromedin U is added, is set as 100%, and an influence on the binding between Neuromedin U and TGR-1 can be calculated. A test compound which makes the inositol triphosphate production activity, for example, 50% or less can be selected as a candidate substance that is capable of altering the binding property between TGR-1 and Neuromedin U. On the other hand, by observing the increase in the inositol triphosphate production activity by single administration of the test compound, an agonist can be screened.

[7] The DNA containing TRE (TPA response element) is inserted into the multi-cloning site upstream of luciferase gene of Picagene basic vector or Picagene enhancer vector (Toyo Ink). It is named as TRE-reporter gene vector. In the cell transfected with the TRE-reporter gene vector, a stimulation which causes the increase in intracellular $Ca^{2+}$ induces an expression of luciferase gene through TRE and a production of luciferase protein. By measuring the luciferase activity, it is possible to detect the change in the amount of intracellular calcium in the cells into which the TRE-reporter gene vector is introduced. The details of the screening method of the compound that alters the binding between Neuromedin U and TGR-1 using the TGR-1-expressing cells to which TRE-reporter gene vector is transfected are as follows.

The TRE-reporter gene introduced TGR-1-expressing cells are placed in a 24-well plate at $5\times10^3$ cell/well, and cultivated for about 48 hours. The cells are washed with Hanks' buffer (pH7.4) containing 0.05% BSA and 20 mM HEPES. 10 nM Neuromedin or 10 nM Neuromedin U and a test compound are added thereto. Then, the reaction is made at 37° C. for 60 minutes. The cells are dissolved in a decomposition solution for Picagene (Toyo Ink). To the decomposition solution, a luminescence substance (Toyo Ink) is added. The luminescence by luciferases can be measured with a luminometer, a liquid scintillation counter, a top counter or the like. An influence of the compound that alters the binding property of Neuromedin U and TGR-1 can be measured by comparing the luminescence by luciferases with that when Neuromedin U is singly administrated. In this process, by administrating Neuromedin U, the amount of luminescence increases through the increase in intracellular $Ca^{2+}$. The compound that inhibits the increase may be selected as a candidate substance that alters the binding property between Neuromedin U and TGR-1. On the other hand, an agonist can be screened by adding the test compound singly and observing the increase in luminescence like the increase by Neuromedin U.

Alkaline phosphatase, chloramphenicol, acyltransferase or β-galactosidase can be used as a reporter gene, besides luciferase. The activity of the product of reporter gene can be measured easily using commercially available measuring kit. The activity of alkaline phosphatase can be measured by Lumi-Phos 530 (Wako); the activity of Chloramphenicol and acetyltransferase can be measured by FAST CAT chrolamphenicol Acetyltransferase Assay Kit (Wako); and the activity of β-galactosidase can be measured by Aurora Gal-XE (Wako).

[8] If the growth of TGR-1-expressing cells in response to Neuromedin U through the activation of MAP kinase can be observed, this growth can be quantified by measuring the activation of MAP kinase, thymidine incorporation, number of cells (e.g. MTT). Using these measurements, the compound that alters the binding between TGR-1 and Neuromedin U can be screened.

After adding Neuromedin U or Neuromedin U and a test compound to the cells, and then obtaining MAP kinase fraction from a decomposed cell solution by immunoprecipitation with an anti-MAP kinase antibody, MAP kinase activity can be measured easily by using, for example, MAP Kinase Assay Kit (Wako) and $\gamma$-[$^{32}$P]-ATP. For thymidine incorporation activity, Neuromedin U or Neuromedin U and the test compound are added to the inoculated TGR-1-expressing cells. Then, [methyl-$^3$H]-thymidine is added thereto. A radioactivity of a labeled thymidine that is taken up into the cells can be measured by dissolving the cells and counting the radioactivity with a liquid scintillation counter.

To measure the growth of TGR-1-expressing cells, the cells are inoculated at first, and then Neuromedin U or Neuromedin U and the test compound are added to the cells. Then, MTT (3-(4,5-dimethyl-2-thiazolyl)-2,5-diphenyl-2H-tetrazolium bromide) is added thereto. After dissolving the cells in iso-propanol which acidified by hydrochloric acid, MTT fromazan which is formed from MTT in the cells was measured by absorption at 570 nm.

The details of screening method using the labeled thymidine incorporation activity for the compound that alters the binding between TGR-1 and Neuromedin U are as follows.

TGR-1-expressing cells are placed at $5\times10^3$ cell/well on a 24-well plate and cultivated for a day. Then, the cells are cultivated in the medium without serum to make the cells to become starved condition. Neuromedin U or Neuromedin U and a test compound are added to the cells and the cells are cultivated for 24 hours. [methyl-$^3$H]-thymidine at 0.015 MBq/well is added thereto and the cells are cultivated for 6 hours. The cells are washed with PBS(−), methanol is added thereto and kept still for 10 minutes. Then, 5% trichloro acetate was added and kept still for 15 minutes. The fixed cells are washed with distilled water 4 times. The cells are dissolved in 0.3 N sodium hydroxide. A radioactivity in the decomposed cell solution is measured with a liquid scintillation counter. An influence of the compound that alters the binding between Neuromedin U and TGR-1 can be measured by comparing the increase in the radioactivity in thymidine incorporation with the case with the single administration of Neuromedin U. The compound that inhibits the increase in the radioactivity by Neuromedin U administration can be selected as a candidate substance that is capable of altering the binding property between Neuromedin U and TGR-1. On the other hand, by administrating the test compound singly and observing the increase in the radioactivity like that with Neuromedin U, an agonist can be screened.

[9] On adding Neuromedin U to TGR-1-expressing cells, K-channel becomes activated, and K ions in the cells flow out of the cells. At this time, Rb ions which belong to the related element, flow out of the cells through K channel as well as K ions. A labeled Rb ([$^{86}$RB]) is added to the cells to make the cells incorporate it. Then, by measuring the efflux of [$^{86}$RB], the activity of Neuromedin U can be measured. The details of screening method for the compound that alters the binding between Neuromedin U and TGR-1 by using the efflux activity of [$^{86}$RB] are as follows.

Two days after placing in a 24-well plate, TGR-1-expressing cells are kept warm for 2 hours in the medium containing $^{86}$RBCl (1 mCi/ml). The cells were washed well to remove $^{86}$RBCl completely from the extracellular solution. Neuromedin U or Neuromedin U and a test compound are added to the cells, and the extracellular solution is collected after 30 minutes. A radioactivity therein is measured by a $\gamma$-counter. An influence of the compound that alters the binding between Neuromedin U and TGR-1 can be measured by comparing the increase in the radioactivity by efflux of [$^{86}$RB] with the case of a single administration of Neuromedin U. The compound that inhibits the increase in the radioactivity by administrating Neuromedin U, can be selected as a candidate substance that is capable of altering the binding property between Neuromedin U and TGR-1.

On the other hand, by administrating the test compound singly and by observing the increase in the radioactivity like that by Neuromedin U, an agonist can be screened.

[10] TGR-1-expressing cells changes extracellular pH (acidification rate) in response to Neuromedin U. By measuring such change with a site sensor device (Molecular Device), the activity of Neuromedin U can be measured. The details of screening method for the compound that alters the binding between Neuromedin U and TGR-1 by measuring the extracellular pH change with the site sensor device are as follows.

TGR-1-expressing cells are cultivated in a capsule of the site sensor over night. The cells are set to the chamber of the device and they are refluxed with RMPI1640 medium supplemented with 0.1% BSA (Molecular Divice) for 2 hours until the extracellular pH become stable. After the pH becomes stable, measured is the pH change of the medium caused by refluxing the medium containing Neuromedin U or Neuromedin U and a test compound on the cells. An influence of the compound that alter the binding of Neuromedin U and TGR-1 can be measured by comparing the change of extracellular pH in TGR-1-expressing cells with that by the single administration of Neuromedin U. The compound that inhibits the change of extracellular pH by administrating Neuromedin U can be selected as a candidate substance that is capable of altering the binding property between Neuromedin U and TGR-1. On the other hand, by administrating the test compound singly and observing the extracellular pH change like that by Neuromedin U, an agonist can be screened.

[11] A sex pheromone receptor STe2 of haploid α-mating Type (MAT α) of yeast (*Saccharomyces cerevisiae*) is coupled with G-protein Gpa1. In response to sex pheromone α-mating factor, the receptor activates MAP kinase, and sequentially Far1 (cell-cycle arrest) and transcription activation factor Ste12. Ste12 induces the expression of various proteins related to the mating, including FUSI. On the other hand, the regulatory factor Sst2 works in an inhibitory manner in the above process. In this system, yeast into which the receptor gene is introduced is prepared. The intracellular signal transduction system in the yeast is activated by a receptor agonist stimulation, and an experiment for the measurement system of the reaction between the receptor agonist and the receptor is conducted by using the growth, etc. resulted from the activation of the intracellular signal transduction as an index (Pausch, M. H., Treinds in Biotechnology, vol.15, pp. 487–494 (1997)). Using such system of the receptor gene introduced yeast, the compound that alters the binding between Neuromedin U and TGR-1 can be screened.

The genes encoding Ste2 and Gpa1 of MATα yeast are removed and the genes encoding TGR-1 and Gpa1-Gai2 fused protein are introduced instead. The gene encoding Far is removed to prevent cell cycle arrest and the gene encoding Sst is removed to increase the sensitivity of response to Neuromedin U. Moreover, the FUS1-H1S3 gene in which FUS1 is connected with a histidine biosynthesis gene HIS3 is introduced. The above-mentioned genetic recombinant method can be easily carried out according to, for example, the method reported by Price (Price, L. A. et al., Molecular and Cellular Biology, vol. 15, pp.6188–6195 (1995)), using TGR-1 gene in place of a somatostatin receptor type 2 (SSTR2). The transformant of yeast constructed according to the above-mentioned method reacts to Neuromedin U that is a ligand of TGR-1 with a high sensitivity, causing the activation of MAP kinase and production of a histidine biosynthetic enzyme so that it can grow in a histidine deficient medium. Using this system, the response of TGR-1 expressing yeast to Neuromedin U can be observed by using the growth of yeast in the histidine deficient medium as an index. The screening method for the compound that alters the binding between Neuromedin U and TGR-1 is as follows.

The above-prepared transformant of yeast is cultured in a complete synthetic medium liquid overnight, added at a concentration of $2 \times 10^4$ cell/ml to a melted agar from which histidine is removed, and plated on square Petri dish (9×9 cm). After the agar becomes hard, a sterilized filter paper absorbing Neuromedin U or Neuromedin U and a test compound, is placed on the surface of agar and the transformant is cultured for 3 days at 30° C. An influence of the compound that alters the binding of Neuromedin U and TGR-1 can be measured by comparing the growth of yeast around the filter paper with the case of singl administration of Neuromedin U. The compound that inhibits the growth of yeast by Neuromedin U administration can be selected as a candidate substance that is capable of altering the binding property of Neuromedin U and TGR-1. On the other hand, an agonist can be screened by administrating only the test compound and observing the growth of yeast like the growth observed in Neuromedin U administration. Furthermore, the transformant of yeast is cultured on the agar containing Neuromedin U, and by observing an influence on the growth of yeast over the surface in Petri dish around the filter paper absorbing a test compound, an influence of the compound that alters the binding of Neuromedin U and TGR-1 can be measured.

[12] An oocyte of *Xenopus Laevis* is injected with RNA of TGR-1 gene and stimulated by Neuromedin U. As a result, intracellular $Ca^{2+}$ concentration increases and calcium-activated chloride current occurs. This change can be detected as a change of membrane potential (similar to the case where K ion concentration gradient is changed). By observing the reaction caused in the TGR-1-introduced *Xenopus Laevis* oocytes by Neuromedin U, the compound that has an influence on the binding between Neuromedin U and TGR-1 can be screened.

A block of oocytes, collected from a female *Xenopus Laevis* numbed by ice-cooling, was treated with collagenase (0.5 mg/ml) dissolved in MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES, pH 7.4), shaking at 150 rpm for 1–6 hours at 19° C. until the block of cells gets loose. After washing for three times with MBS, TGR-1 mRNA (50 ng/50 nl) is microinjected into an oocyte with a micromanipulator. TGR-1 mRNA can be prepared from tissues or cells, or by in vitro transcription from a plasmid. The oocyte is cultured in MBS solution for 3 days at 20° C., and placed in a pit of a voltage clamp devise where Ringer solution flows. Glass microelectrodes for voltage clamp and voltmeter are inserted into the cell and the cathode is placed outside of the cell. After the potential become stable, the change in potential is recorded after passing the Ringer solution containing Neuromedin U or Neuromedin U and a test compound. An influence of the compound that alters the binding between Neuromedin U and TGR-1 is measured by comparing the membrane potential change of TGR-1 introduced *Xenopus Laevis* oocyte with the case of single administration of Neuromedin U. The compound that inhibits the cell membrane potential change can be selected as a candidate substance that is capable of altering the binding between TGR-1 and Neuromedin U. On the other hand, an agonist can be screened by administrating only the test compound and observing the cell membrane potential change like the change observed in Neuromedin U administration.

In this system, poly (A)+ RNA of various G-protein genes can be introduced to amplify the change so that the reaction can be measured easily. Also, the poly (A)+ RNA of protein gene, such as aequorin which radiates light in the presence of Ca ion is injected as well so that the reaction can be measured by observing the radiation of light instead of the membrane potential change.

The screening kit for a compound or a salt thereof that alters the binding property of Neuromedin U with TGR-1 comprises TGR-1, the cells containing TGR-1, or the membrane fraction of the cells containing TGR-1; and Neuromedin U.

Examples of the screening kit of the present invention are as follows.

1. Reagents for Screening:

(1) Buffer for Measurement and Washing

Hanks' balanced salt solution (Gibco Co.) supplemented with 0.05% bovine serum albumin (Sigma Co.).

The solution is sterilized by filtration through a 0.45 μm filter, and stored at 4° C. or may be prepared at use.

(2) Standard TGR-1 Preparation

CHO cells expressing TGR-1 which are plated on a 12-well plate at a density of $5 \times 10^5$ cells/well, and cultured at 37° C. under 5% $CO_2$ and 95% air for 2 days.

(3) Labeled Ligands

Neuromedin U labeled with $[^3H]$, $[^{125}I]$, $[^{14}C]$, $[^{35}S]$ etc., which is dissolved in an appropriate buffer, and stored at 4° C. or −20° C., and diluted to 1 μM with the measurement buffer at use.

(4) Standard Ligand Solution

Neuromedin U is dissolved in PBS containing 0.1% bovine serum albumin (Sigma Co.) at a final concentration of 1 mM, and stored at −20° C.

2. Measurement Method:

(1) TGR-1-expressing cells are cultured in a 12-well culture plate and washed twice with 1 ml of the measurement buffer, and 490 μl of the measurement buffer is added to each well.

(2) After adding 5 μl of $10^{-3}$–$10^{-10}$ M test compound solution, and then 5 μl of a labeled Neuromedin U, the cells are incubated at room temperature for an hour. To determine the amount of the non-specific binding, 5 μl of $10^{-3}$ M Neuromedin U is added in place of the test compound.

(3) The reaction solution is removed, and the wells are washed 3 times with the washing buffer. The labeled Neuromedin U bound to the cells is dissolved in 0.2N NaOH-1% SDS, and mixed with 4 ml of liquid scintillator A (Wako Pure Chemical Industries, Ltd.)

(4) The radioactivity is measured using a liquid scintillation counter (Beckman Co.), and the percent maximum binding (PMB) is calculated by the equation below.

$$PMB = [(B-NSB)/(B_0-NSB)] \times 100$$

PMB: Percent maximum binding
B: Value obtained in the presence of a test compound
NSB: Non-specific binding
$B_0$: Maximum binding The compound obtained by the screening method or the screening kit of the present invention, or a salt thereof is a compound that alters (inhibits or enhances) the binding between Neuromedin U and TGR-1. Concretely, it is a compound having the TGR-1-mediated cell stimulating activity (so-called TGR-1 agonist) or a compound not having the cell stimulating activity (so-called TGR-1 antagonist). The compounds include peptides, proteins, non-peptide compounds, synthetic compounds, and fermentation products. They may be novel or known compounds.

The evaluation method for determining whether it is the TGR-1 agonist or TGR-1 antagonist mentioned above is described in (i) and (ii) below.

(i) By conducting binding assay according to the screening methods (1)–(3) above, the compound that alters (especially, inhibits) the binding property between Neuromedin U and TGR-1 is obtained. Then, the obtained compound is assayed as to whether it has the above-mentioned TGR-1-mediated cell stimulating activities or not. The compound having the cell stimulating activities or a salt thereof is determined to be a TGR-1 agonist, and the compound not having the cell stimulating activities or a salt thereof is determined to be a TGR-1 antagonist.

(ii)(a) The above-mentioned TGR-1-mediated cell-stimulating activity is measured after contacting a test compound to cells having TGR-1. The compound having the cell stimulating activity or salt thereof is a TGR-1 agonist.

(b) The above-mentioned TGR-1-mediated cell-stimulating activity is measured and compared between when the compound that activates TGR-1 (e.g. Neuromedin U or TGR-1 agonist) is brought in contact with cells having TGR-1 and when the compound that activates TGR-1 and the test compound are brought in contact with cells having TGR-1. The compound or a salt thereof which may reduce the cell stimulating activity induced by the compound that activates TGR-1 is a TGR-1 antagonist.

Since TGR-1 agonists have the same physiological activities as that of Neuromedin U, they are useful as safe and low-toxic pharmaceuticals.

On the other hand, since TGR-1 antagonists can inhibit the physiological activities of Neuromedin U, they are useful as safe and low-toxic pharmaceuticals for inhibiting the receptor activities.

Since Neuromedin U or a salt thereof relates to the smooth muscle contraction, the increase in blood pressure, the regulation of ion-transportation in intestine, and the increase in ACTH and subsequent increase in corticosterone after its hypodermic administration, it can be used as a prophylactic and/or therapeutic agent for hypotension, and a local vasoconstrictor. Thus, among compounds obtainable by the above-mentioned screening methods or screening kits, TGR-1 agonists can be useful as a prophylactic and/or therapeutic agent for hypotension, a local vasoconstrictor, and further be useful as a uterine contraction accelerating agent for ameliorating, preventing and treating various diseases associated with uterine contraction insufficiency, such as weak labor contraction, atonic bleeding, delivery of the placenta, uterine involution insufficiency, artificial abortion, induction of delivery, arrest of delivery, endocervical canal asthenia, inversion of the uterus, retention of the placenta and egg membrane, postpartum hemorrhage, prolapse of the muliebria, infertility, care for mother's body at multiple pregnancy, malpresentation, dysmenorrhea, miscarriage, endometriosis, chronic inflammatory disease of the uterus, myoma of the uterus, deformity of the uterus, adenomyosis of the uterus, uterocervical laceration, post-traumatic stress syndrome.

TGR-1 antagonists can be useful as a prophylactic and/or therapeutic agent for hypertension, myocardial dysfunction, acute renal failure, stress-related diseases, for example, (1) diseases of cardiovascular system (angina pectoris, myocardial infarction, arrhythmia, etc.), (2) diseases of respiratory system (bronchial asthma, hyperpnea syndrome, etc.), (3)

diseases of musculoskeletal system (e.g. chronic arthorheumatism, lumbago, migraine, tension headache, etc.), (4) other diseases (e.g. diabetes, climacteric disorder, chronic pain, decrease of immunity, etc.), diseases of digestive system (gastric ulcer, ulcerative colitis, etc). Further, TGR-1 antagonists are useful as a uterine contraction suppressing agent for ameliorating, preventing and treating various diseases associated with excessive uterine contraction, such as too strong contraction, pseudo-contraction, prolonged pregnancy, tonic uterine contraction, fetal asphyxia, uterine rupture, endocervical canal laceration, premature delivery, myoma of the uterus, deformity of uterus, adenomyosis of the uterus, abnormal expulsive force, chronic inflammatory disease of the uterus, care for mother's body at multiple pregnancy, malpresentation, Prader-Willi syndrom, dysmenorrhea.

Moreover, since Neuromedin U and a salt thereof has the function of controlling appetite, among compounds obtainable by the above-mentioned screening methods or screening kits on the basis of said function, TGR-1 agonists are used as anorectic agents, anti-adiposis agents, remedies for bulimia and polyphagia, and TGR-1 antagonists are used as aperitive agents.

For the salt of the compound that can be obtained according to the above-mentioned screening method or the screening kit, for example, the pharmacologically acceptable salt is used. The examples are a salt with an inorganic base, a salt with an organic base, a salt with an inorganic acid, a salt with an organic acid, a salt with a basic or acidic amino acid and so on.

The preferred examples of salt with an inorganic base include an alkali metal salt such as sodium salt, potassium salt; alkali earth metal salt, calcium salt and magnesium salt; and aluminum salt, ammonium salt, etc.

The preferred examples of salt with an organic base include trimethylamine salt, triethylamine salt, pyridine salt, picoline salt, 2,6-lutidine salt, ethanolamine salt, diethanolamine salt, triethanolamine salt, cyclohexylamine salt, dicyclohexylamine salt, N,N'-dibenzylethylenediamine salt, etc.

The preferred examples of salt with an inorganic acid are hydrochloric acid salt, hydrobromic acid salt, sulfuric acid salt, phosphoric acid salt, etc.

The preferred examples of salt with an organic acid are formic acid salt, acetic acid salt, propionic acid salt, fumaric acid salt, oxalic acid salt, tartaric acid salt, maleic acid salt, citric acid salt, succinic acid salt, malic acid salt, methanesulfonic acid salt, benzenesulfonic acid salt, benzoic acid salt, etc.

The preferred examples of salt with a basic amino acid include a salt with arginine, lysine, ornithine, etc. The preferred examples of salt with an acidic amino acid include a salt with aspartic acid, glutamic acid, etc.

When the compound obtainable using the screening method or the screening kit or a salt thereof is used as the above-mentioned drug, it can be used as follows.

When the compound obtainable using the screening method or the screening kit or a salt thereof is used as the above-mentioned drug, it can be prepared by publicly known methods. For example, the compound can be used orally as tablets having sugar coating or enteric coating as necessary, capsules, elixirs and microcapsules, or parenterally as an injection, such as an aseptic solution or suspension with water or other pharmaceutically acceptable. For example, these preparations can be produced by admixing physiologically acceptable carriers, flavors, excipients, vehicles, preservatives, stabilizers and binders with the compound or a salt thereof of the present invention in a generally acceptable unit dose required for pharmaceutical formulation. The amount of the active ingredient in these pharmaceutical preparations is designed to have a suitable dose in the designated range.

The additives which can be admixed in the tablets, capsules etc. include, for example, binders such as gelatin, corn starch, tragacanth, gum arabic; excipients such as crystalline cellulose; swelling agents such as corn starch, gelatin and alginic acid; lubricants such as magnesium stearate; sweeteners such as sucrose, lactose and saccharine; and flavors such as peppermint, akamono oil and cherry. When a capsule is in a unit dosage form, liquid carriers such as fats and oils can be contained in the materials described above. The aseptic composition for injection can be formulated according to conventional pharmaceutical formulation by dissolving or suspending the active material and naturally occurring vegetable oils such as sesame oil and coconut oil in vehicles such as injection water.

The aqueous liquid for injection includes, for example, physiological saline or an isotonic solution containing glucose and other supplementary agents (e.g., D-sorbitol, D-mannitol, sodium chloride etc.), and may be used in combination with suitable solubilizer such as alcohols (e.g., ethanol etc.), polyalcohols (e.g., propylene glycol, polyethylene glycol etc.) and nonionic surfactants (e.g., Polysorbate 80™, HCO-50 etc.). The oily liquid includes, for example, sesame oil, soybean oil etc., and may be used in combination with solubilizer such as benzyl benzoate, benzyl alcohol etc.

Further, it may contain buffers (e.g., phosphate buffer, sodium acetate buffer etc.), soothing agents (e.g., benzalkonium chloride, procaine hydrochloride etc.), stabilizers (e.g., human serum albumin, polyethylene glycol etc.), preservatives (e.g., benzyl alcohol, phenol etc.), antioxidants etc. Usually, the prepared injection is filled into suitable ampoules.

The pharmaceutical preparation thus obtained is safe and low toxic so that it can be administered to warm-blooded animals (e.g., human, guinea pig, rat, mouse, pig, sheep, cow, monkey, dog and chicken), amphibian (e.g. frog) and fish.

Dose of the compound or a salt thereof (especially antagonists) which is obtained by the screening method or the screening kit of the present invention will vary depending on conditions. In oral administration to an adult patient (60 kg body weight) with hypertension, the dose is normally about 0.1 to 1000 mg, preferably about 1.0 to 300 mg, and more preferably about 3.0 to 50 mg per day. In parenteral administration, the single dose will also vary depending on subject to be administered, conditions, routes for administration, etc. For example, in an injection form for an adult patient with hypertension (60 kg body weight), advantageously, a daily dose of about 0.01 to 30 mg, preferably about 0.1 to 20 mg, and more preferably about 0.1 to 10 mg will be administered intravenously. For other animal species, the dose to be administered can also be calculated according to its body weight from the dose for 60 kg body weight.

The present invention further relates to an antibody to TGR-1.

The antibody to TGR-1 may be any polyclonal or monoclonal antibody which is capable of recognizing TGR-1.

The antibody to TGR-1 may be produced by a well-known method for producing an antibody or antisera, using as TGR-1 the antigen.

[Preparation of Monoclonal Antibody]

(a) Preparation of Monoclonal Antibody-Producing Cells

TGR-1 is administered to warm-blooded animals either solely or together with carriers or diluents to the site where the production of antibody is possible by the administration. In order to potentiate the antibody productivity upon the administration, complete Freund's adjuvant or incomplete Freund's adjuvant may be administered. The administration is usually carried out once every two to six weeks and two to ten times in total. Examples of the applicable warm-blooded animals are monkeys, rabbits, dogs, guinea pigs, mice, rats, sheep and goats, with the use of mice and rats being preferred.

In the preparation of monoclonal antibody-producing cells, warm-blooded animals, e.g. mice are immunized with an antigen, a individual having detectable antibody titer is selected, then spleen or lymph node is collected after two to five days after the final immunization, and antibody-producing cells contained therein are fused with myeloma cells to give monoclonal antibody-producing hybridomas. Measurement of the antibody titer in antisera may be carried out, for example, by reacting a labeled TGR-1 with the antiserum, followed by assaying the binding activity of the label bound to the antibody. The fusion may be carried out, for example, by the known method by Koehler and Milstein (Nature, 256, 495, 1975). Examples of the fusion accelerator are polyethylene glycol (PEG), Sendai virus, etc., of which PEG is preferably employed.

Examples of the myeloma cells are NS-1, P3U1, SP2/0, AP-1, etc. P3U1 is preferably employed. A preferred ratio of the number of the antibody-producing cells used (spleen cells) to the number of myeloma cells is within a range of approximately 1:1 to 20:1. When PEG (preferably, PEG 1000 to PEG 6000) is added in a concentration of approximately 10 to 80% followed by incubating at 20 to 40° C., preferably at 30 to 37° C. for 1 to 10 minutes, an efficient cell fusion can be carried out.

Various methods can be used for screening a monoclonal antibody-producing hybridoma. Examples of such methods include a method which comprises adding the supernatant of hybridoma to a solid phase (e.g., microplate) adsorbing TGR-1 antigen directly or together with a carrier, adding an anti-immunoglobulin antibody (where mouse cells are used for the cell fusion, anti-mouse immunoglobulin antibody is used) labeled with a radioactive substance or an enzyme or Protein A, and detecting the monoclonal antibody bound to the solid phase; and a method which comprises adding the supernatant of hybridoma to a solid phase adsorbing an anti-immunoglobulin antibody or Protein A, adding TGR-1 labeled with a radioactive substance or an enzyme, and detecting the monoclonal antibody bound to the solid phase.

The monoclonal antibody can be selected according to publicly known methods or their modifications. In general, the selection can be effected in a medium for animal cell supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out in the same way as the case of a polyclonal antibody, by conventional methods for separation and purification of immunoglobulins (for example, salting-out, alcohol precipitation, isoelectric point precipitation, electrophoresis, adsorption and desorption with ion exchangers (e.g. DEAE), ultracentrifugation, gel filtration, or a affinity purification method which comprises collecting only an antibody with an activated adsorbent such as an antigen-binding solid phase, Protein A or Protein G, and dissociating the binding to obtain the antibody.

[Preparation of Polyclonal Antibody]

The polyclonal antibody of the present invention can be produced by publicly known methods or modifications thereof. For example, a warm-blooded animal is immunized with the complex of the immunogen (TGR-1) and a carrier protein in a manner similar to the method described above for the production of monoclonal antibodies. The fraction containing the antibody to TGR-1 is collected from the immunized animal to carry out separation and purification of the antibody.

In the complex of immunogen and carrier protein used to immunize a warm-blooded animal, any type of carrier protein may be crosslinked to the hapten in any mixing ratio of carrier to hapten, as long as the antibody is efficiently produced to the immunized complex. For example, bovine serum albumin, bovine thyroglobulin or keyhole limpet hemocyanin, etc. is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every 2 to 6 weeks and 3 to 10 times in total.

The polyclonal antibody can be collected from the blood, ascites, etc., preferably from the blood of warm-blooded animal immunized by the method described above.

The titer of polyclonal antibody in antiserum can be assayed by the same procedure as that for the determination of titer of serum antibody described above. The separation and purification of the polyclonal antibody can be carried out according to the method for the separation and purification of immunoglobulins as performed in the separation and purification of monoclonal antibodies described above.

The antibody of the present invention is capable of recognizing specifically TGR-1. Therefore, the antibody can be used to quantify TGR-1 in a test fluid, especially by the sandwich immunoassay, etc. Thus, the present invention provides, for example, the following quantification methods:

(i) a method of quantifying TGR-1 in a test fluid, which comprises reacting the antibody of the present invention competitively with the test fluid and the labeled TGR-1; and measuring the ratio of the labeled TGR-1 bound to the antibody; and, (ii) a method of quantifying TGR-1 in a test fluid, which comprises reacting the test fluid with the antibody of the present invention immobilized on a carrier and the labeled antibody of the present invention simultaneously or sequentially; and measuring the activity of the label on the immobilizing carrier.

In (ii) described above, it is preferred that one antibody recognizes the N-terminal region of TGR-1, and the other antibody reacts with the C-terminal region of TGR-1.

Using the monoclonal antibody to TGR-l (hereinafter sometimes referred to as the monoclonal antibody of the present invention), TGR-1 can be assayed and also detected by tissue staining. For this purpose, an antibody molecule itself may be used, or $F(ab')_2$, Fab' or Fab fractions of the antibody molecule may also be used. Assay methods using the antibody to TGR-1 are not particularly limited. Any assay method can be used, so long as the amount of antibody, antigen, or antibody-antigen complex corresponding to the amount of antigen (e.g., the amount of TGR-1) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, $[^{125}I]$, $[^{131}I]$, $[^3H]$ and $[^{14}C]$ are used. As the enzyme described above, stable enzymes with high specific activity are preferred; for example, β-galactosidase, β-glucosidase, alkaline phosphatase, peroxidase, malate dehydrogenase and the like are used. Examples of the fluorescent substance used are fluorescamine and fluorescein isothiocyanate. For the luminescent substance, for example, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of proteins or enzymes may also be used. For the carrier, for example, insoluble polysaccharides such as agarose, dextran, cellulose, etc.; synthetic resin such as polystyrene, polyacrylamide, silicon, etc., and glass or the like are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of TGR-1 in the test fluid can be quantified. The order of the primary and secondary reactions may be reversed, and the reactions may be performed simultaneously or with an interval. The labeling agent and method for immobilization may be the same as those described above.

In the sandwich immunoassay, the immobilized or labeled antibody is not necessarily based on one type of antibody, but a mixture of two or more types of antibodies may be used to improve assay sensitivity or the like.

In the sandwich assay for measuring TGR-1, the monoclonal antibodies of the present invention which bind to different sites of TGR-1 are preferably used in the first and second reactions. Thus, as to the antibodies used in the first and second reactions, for example, when the antibody used in the second reaction recognizes the C-terminal region of TGR-1, it is preferable to use the antibody recognizing regions other than the C-terminal region, e.g., the N-terminal region in the first reaction.

The monoclonal antibody of the present invention can be used for assay systems other than the sandwich method, for example, the competitive method, immunometric method, nephrometry, etc. In the competitive method, antigen in a test fluid and the labeled antigen are competitively reacted with antibody, and the unreacted labeled antigen (F) and the labeled antigen bound to the antibody (B) are separated (B/F separation). By measuring the amount of the label in B or F, the amount of the antigen in the test fluid is determined. The above reaction method includes a liquid phase method using an antibody in a soluble form, polyethylene glycol for B/F separation and a secondary antibody to the soluble antibody; and an solid phase method either using the immobilized primary antibody, or using the soluble primary antibody and the immobilized secondary antibody.

In the immunometric method, after reacting antigen in a test fluid and immobilized antigen competitively with a definite amount of labeled antibody, the solid phase is separated from the liquid phase. Alternatively, after reacting antigen in a test fluid with an excess amount of labeled antibody, and then adding immobilized antigen to adsorb the unreacted labeled antibody, the solid phase is separated from the liquid phase. Then, the amount of the label in either phase is measured to quantify the antigen in the test fluid.

In the nephrometry, an insoluble precipitate produced after the antigen-antibody reaction in gel or solution is quantified. When the amount of antigen in the test fluid is so small that only a small amount of precipitate is obtained, laser nephrometry using scattering of laser is advantageously employed.

For applying these immunological methods to the measuring methods of the present invention, any particular conditions or procedures are not required. Systems for measuring the rat TGR-1 of the present invention or its salts are constructed by adding the usual technical consideration in the art to the conventional conditions and procedures. For the details of these general technical means, reference can be made to the following reviews and texts. See, for example, Hiroshi Irie, ed. "Radioimmunoassay" (Kodansha, published in 1974); Hiroshi Irie, ed. "Sequel to the Radioimmunoassay" (Kodansha, published in 1979); Eiji Ishikawa, et al. ed. "Enzyme immonoassay" (Igakushoin, published in 1978); Eiji Ishikawa, et al. ed. "Immunoenzyme assay" (2nd ed.) (Igakushoin, published in 1982); Eiji Ishikawa, et al. ed. "Immunoenzyme assay" (3rd ed.) (Igakushoin, published in 1987); Methods in ENZYMOLOGY, Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies))(all published by Academic Press Publishing).

In this way, TGR-1 can be quantified in high sensitivity using the antibody of the present invention.

Further, it is possible to conduct diagnosis on various diseases which are associated with dysfunction of TGR-1 through quantification of TGR-1 in vivo using the antibody of the present invention.

The antibody of the present invention can also be used for specific detection of TGR-1 present in test samples, such as body fluids or tissues. The antibody may also be used for preparation of antibody columns for purification of TGR-1, for detection of TGR-1 in fractions upon purification, and for analysis of the behavior of TGR-1 in the test cells.

In the specification and drawings, nucleic acids and amino acids are denoted in accordance with the IUPAC-IUB Commission on Biochemical Nomenclature or the conventional manner in the art, examples of which are shown below. The optical isomer of amino acid is L form unless otherwise indicated.

DNA: deoxyribonucleic acid
cDNA: complementary deoxyribonucleic acid
A: adenine
T: thymine
G: guanine
C: cytosine
Y: thymine or cytosine
N: adenine, guanine, cytosine or thymine
R: adenine or guanine
M: adenine or cytosine
W: adenine or thymine
S: guanine or cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
TFA: trifluoroacetic acid
EIA: enzyme immunoassay
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid
Me: methyl
Et: ethyl
Bu: butyl
Ph: phenyl
TC: thiazolidine-4(R)-carboxamide
Bom: benzyloxymethyl
NMP: N-methylpyrrolidone
PAM: phenylacetoamidemethyl The substituents, protective groups and reagents, which are frequently used in the specification, are shown by the following abbreviations.

Tos: p-toluenesulfonyl
HONB: 1-hydroxy-5-norbornene-2,3-dicarboximide
Bzl: benzyl
Z: benzyloxycarbonyl
Br-Z: 2-bromobenzyloxycarbonyl
Cl-Z: 2-chlorobenzyloxycarbonyl
Boc: t-butoxycarbonyl
HOBt: 1-hydroxybenztriazole
DCC: N,N'-dicyclohexylcarbodiimide
TFA: trifluoroacetic acid
Fmoc: N-9-fluorenylmethoxycarbonyl
DNP: dinitrophenyl
Bum: t-butoxymethyl
Trt: trityl
BSA: bovine serum albumin
CHAPS: 3-[(3-colamidepropyl)dimethylanmmonio]-1-propane sulfonate
PMSF: phenylmethylsulfonylfluoride
E64: (L-3-trans-caroboxoirane-2-carbonyl) L-leucyl-agumatin
GDP: Guanosine-5'-diphosphate
MEM á: minimum essential medium alpha
Fura-2AM: 1-[6-amino-2-(5-carboxy-2-oxazolyl)-5-benzofuranyloxy]-2-(2-amino-5 methylphenoxy)-ethane-N', N', N', N'-tetra acetic acid-pentacetoxymethyl ester
HBSS: Hanks' Balanced Salt Solution
Fluo-3AM: 1-[2-amino-5-(2,7-dichloro-6-hydroxy-3-oxy-9-xanthenyl)phenoxy]-2-(2-amino-5-methylphenoxy)ethane-N', N',N',N'-tetra acetic acid pentaacetoxymethyl ester
HEPES: 2-[4-(2-hydroxyethyl)-1-piperazinyl]ethanesulfonic acid
MeBzl: 4-methylbenzyl
NMP: N-methylpyrrolidone Each of the sequence identification numbers in the Sequence Listing indicates the following sequence.

[SEQ ID NO:1]
This shows the amino acid sequence of TGR-1 obtained in Example 1.

[SEQ ID NO:2]
This shows the nucleic acid sequence of DNA encoding TGR-1 having the amino acid sequence shown by SEQ ID NO:1.

[SEQ ID NO:3]
This shows the nucleic acid sequence of primer 1 described in Example 1.

[SEQ ID NO:4]
This shows the nucleic acid sequence of primer 2 described in Example 1.

[SEQ ID NO:5]
This shows the amino acid sequence of pig Neuromedin U-8.

[SEQ ID NO:6]
This shows the amino acid sequence of dog Neuromedin U-8.

[SEQ ID NO:7]
This shows the amino acid sequence of chicken Neuromedin U-9.

[SEQ ID NO:8]
This shows the amino acid sequence of guinea pig Neuromedin U-9.

[SEQ ID NO:9]
This shows the amino acid sequence of rat Neuromedin U-23.

[SEQ ID NO:10]
This shows the amino acid sequence of frog Neuromedin U-23.

[SEQ ID NO:11]
This shows the amino acid sequence of human Neuromedin U-25.

[SEQ ID NO:12]
This shows the amino acid sequence of pig Neuromedin U-25.

[SEQ ID NO:13]
This shows the amino acid sequence of dog Neuromedin U-25.

[SEQ ID NO:14]
This shows the amino acid sequence of chicken Neuromedin U-25.

[SEQ ID NO:15]
This shows the amino acid sequence of frog Neuromedin U-25.

[SEQ ID NO:16]
This shows an amino acid sequence of a partial peptide of Neuromedin U-25. This corresponds to an amino acid sequence at the 4 to 8 positions in the amino acid sequence shown by SEQ ID NO: 5.

[SEQ ID NO:17]
This shows the amino acid sequence which is substantially the same sequence as TGR-1 (as described in WO 99/55732).

[SEQ ID NO:18]
This shows the nucleic acid sequence of DNA encoding the amino acid sequence shown by SEQ ID NO:23.

[SEQ ID NO:19]
This shows the nucleic acid sequence of the primer RTGRF2 described in Example 3.

[SEQ ID NO:20]
This shows the nucleic acid sequence of the primer RTGRR1 described in Example 3.

[SEQ ID NO:21]
This shows the amino acid sequence of rat TGR-1 obtained in Example 3.

[SEQ ID NO:22]
This shows the nucleic acid sequence of DNA encoding rat TGR-1.

*Escherichia coli* transformant TOP10/pCR2.1TOPO-TGR-1 which has cDNA encoding TGR-1 shown by SEQ ID NO:1 obtained in Example 1 was on deposit with the Ministry of International Trade and Industry, Agency of Industrial Science and Technology, National Institute of Bioscience and Human Technology (NIBH), located at 1-1-3, Higashi, Tsukuba-shi, Ibaraki, Japan, as the Accession Number FERM BP-6964 on Dec. 6, 1999; and with Institute for Fermentation (IFO), located at 2-17-85, Juso Honcho, Yodogawa-ku, Osaka-shi, Osaka, Japan, as the Accession Number IFO 16336 on Nov. 12, 1999.

*Escherichia coli* transformant JM109/prTGR-1 which has cDNA encoding TGR-1 shown by SEQ ID NO:21 obtained in Example 3 was on deposit with the Ministry of International Trade and Industry, Agency of Industrial Science and Technology, National Institute of Bioscience and Human Technology (NIBH), located at 1-1-3, Higashi, Tsukuba-shi, Ibaraki, Japan, as the Accession Number FERM BP-7355 on Nov. 9, 2000; and with Institute for Fermentation (IFO), located at 2-17-85, Juso Honcho, Yodogawa-ku, Osaka-shi, Osaka, Japan, as the Accession Number IFO 16488 on Oct. 24, 2000.

EXAMPLES

The following examples are intended to illustrate the present invention in detail, but not intended to limit the scope of the present invention.

Example 1

Cloning of cDNA Encoding TGR-1 and Determination of its Nucleic Acid Sequence

A PCR was carried out using human testis cDNA (Marathon-Ready™ cDNA; Clontech) as a template, and 2 primers, primer 1 (SEQ ID NO:3) and primer 2 (SEQ ID NO:4). The PCR, using Advantage 2 Polymerase Mixture (Clontech), followed (i) 95° C. for 1 min.; (ii) 5 cycles of 95° C. for 30 sec. and 68° C. for 2 min.; (iii) 5 cycles of 95° C. for 30 sec., 64° C. for 30 sec. and 68° C. for 2 min.; (iv) 30 cycles of 95° C. for 30 sec., 62° C. for 30 sec. and 68° C. for 2 min.; and (v) 68° C. for 7 min. for elongation. After the reaction, the reaction product was subcloned into a plasmid vector pCR2.1TOPO according to the instruction for TA cloning Kit (Invitrogen). The resulting plasmid was introduced into *E. coli* TOP10, and a clone having the plasmid was selected in a LB agar plate containing ampicilin. As a result of analysis of each clonal sequence, cDNA sequence (SEQ ID NO:2) encoding TGR-1 (SEQ ID NO:1) was obtained.

Example 2

Comparison of Neuromedin U-8-Induced Responses in TGR-1-Expressing CHO Cells and Mock CHO Cells by a Site Sensor Technique TGR-1-expressing CHO cells were prepared according to a known method using the cDNA encoding TGR-1, obtained in Example 1. TGR-1-expressing CHO cells and mock CHO cells were plated in the capsules for site sensor at a density of $2.7 \times 10^5$ cells/well, and cultured overnight. The capsules containing the cells were set in the site sensor, and these cells were refluxed with a low-buffered RMPI medium supplemented with 0.1% bovine serum albumin for acclimation. Repeating a pumping cycle of ON (80 seconds) and OFF (40 seconds), a rate of change in extracellular pH was measured as an acidification rate with the site sensor with time of pumping off.

Pig Neuromedin U-8 (BACHEM, H-5505, SEQ ID NO:5) was dissolved in the medium, and the diluted solutions thereof were prepared at the step-wise decreased concentrations. They were exposed to the cells for 7 minutes and 2 seconds through switching the flow paths. As a result of comparing the peak reaction values after corrected setting the values obtained during 3 cycles immediately before the exposure of the dilution to the cells as 100%, it was observed that TGR-1-expressing CHO cells reacted to Neuromedin U in a specific and does-dependent manner (FIG. 1)

Example 3

Obtaining cDNA encoding Rat TGR-1

To obtain a fragment of a full-length cDNA encoding Rat TGR-1, the following 2 kinds of DNAs were synthesized.
RTGRF2:5'-CTGATGCTATCCTTTCACTCTCTCA-GACC-3' (SEQ ID NO:19)
RTGRR1:5'-TCCTTGCAGTTTTGGCACATA-GATGGA-3' (SEQ ID NO:20)

Figure 2:
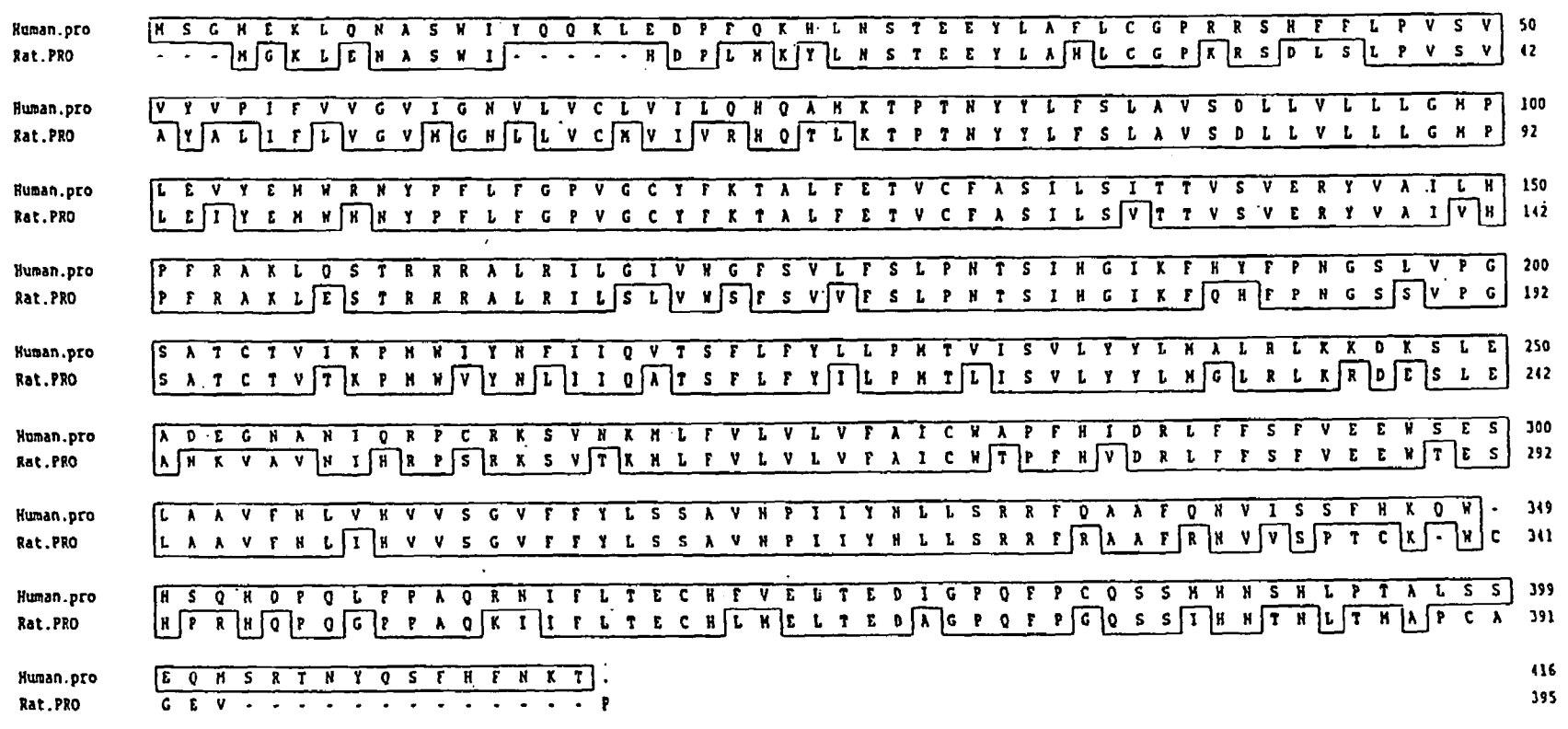

Using these synthetic DNAs, RTGRF2 and RTGRR1 as primers, and cDNAs synthesized from poly(A)⁺RNA of rat uterus as a template, a PCR was carried out to amplify a fragment encoding the full-length cDNA. The reaction solution for the PCR was a total volume 25 µl composed of 2 µl cDNA solution (derived from 8 ng poly(A)⁺ RNA), 1 µl dNTP (10 mM), 0.5 µl Advantage 2 DNA polymerase (Clonetech), 2.5 µl 10× buffer solution attached to the DNA polymerase product, 18 µl distilled water, and 0.5 µl of each RTGRF2 and RTGRR1 (each 10 µM). After heating the reaction solution at 95° C. for 2 minutes for denaturation, the PCR was carried out by repeating 31 times a cycle of 98° C. for 10 seconds and 65° C. for 90 seconds. About 1.4 kb PCR product was detected using electrophoresis, purified using QIA quick Gel Extraction Kit (Quiagen), inserted into the cloning vector pCR2.1TOPO according to the instruction for TA cloning Kit (Invitrogen), and introduced into *E. coli* JM109 to give a transformant *E. coli* JM109/prTGR-1. The nucleic acid sequence inserted in the plasmid prTGR-1 was determined (SEQ ID NO:22), and the amino acid sequence predicted from the coding sequence was shown in SEQ ID NO:21. In addition, FIG. 2 shows comparison of this amino acid sequence with the human sequence (SEQ ID NO:1) obtained in Example 1.

INDUSTRIAL APPLICABILITY

The screening method for a compound or a salt thereof that alters the binding property between Neuromedin U and TGR-1, characterized by using Neuromedin U and TGR-1, can be useful for screening a therapeutic and/or prophylactic agent for obesity, hypertension and stress-related diseases. A TGR-1 agonist can be useful as a therapeutic and/or prophylactic agent for obesity, etc. A TGR-1 antagonist can be useful as a therapeutic and/or prophylactic agent for hypertension and stress-related diseases, etc.

The invention claimed is:

1. A method for screening for a compound or a salt thereof that alters the binding property of Neuromedin U or a salt thereof with a protein or a salt thereof of amino acid sequence SEQ ID NO:1 or SEQ ID NO:21, comprising the steps of:
   a) measuring the binding of a labeled Neuromedin U with said protein or a salt thereof;
   b) measuring the binding of a labeled Neuromedin U with said protein or a salt thereof in the presence of a test compound; and
   c) comparing the results of steps a) and b).

2. The screening method according to claim 1, wherein said Neuromedin U is a peptide of amino acid sequence SEQ ID NO:11.

3. A kit for screening for a compound or a salt thereof that alters the binding property of Neuromedin U or a salt thereof with a protein or a salt thereof of amino acid sequence SEQ ID NO:1 or SEQ ID NO:21, comprising:
   Neuromedin U, a derivative thereof or a salt thereof; and
   a protein or a salt thereof of amino acid sequence SEQ ID NO:1 or SEQ ID NO:21.

4. The screening kit according to claim 3, wherein said Neuromedin U is a peptide of amino acid sequence SEQ ID NO:11.

5. A method for screening for a compound or a salt thereof that alters the binding property of Neuromedin U or a salt thereof with a protein or a salt thereof having an amino acid sequence at least about 90% homologous to SEQ ID NO:1 or SEQ ID NO:21 comprising the steps of:
   a) measuring the binding of a labeled Neuromedin U with said protein or a salt thereof;
   b) measuring the binding of a labeled Neuromedin U with said protein or a salt thereof in the presence of a test compound; and
   c) comparing the results of steps a) and b)
   wherein said protein or salt thereof are activated by Neuromedin U binding.

6. The method of claim 5 wherein said protein has an amino acid sequence at least about 95% homologous to SEQ ID NO:1 or SEQ ID NO:21.

7. The method of claim 5 wherein said protein has an amino acid sequence at least about 98% homologous to SEQ ID NO:1 or SEQ ID NO:21.

8. A kit for screening for a compound or a salt thereof that alters the binding property of Neuromedin U or a salt thereof with a protein or a salt thereof having an amino acid sequence at least about 90% homologous to SEQ ID NO:1 or SEQ ID NO:21 comprising:
   Neuromedin U, a derivative thereof or a salt thereof; and
   a protein or a salt thereof having an amino acid sequence at least about 90% homologous to SEQ ID NO:1 or SEQ ID NO:21 wherein said protein or salt thereof are activated by Neuromedin U binding.

9. The kit of claim 8 wherein said protein has an amino acid sequence at least about 95% homologous to SEQ ID NO:1 or SEQ ID NO:21.

10. The kit of claim 8 wherein said protein has an amino acid sequence at least about 98% homologous to SEQ ID NO:1 or SEQ ID NO:2.

* * * * *